United States Patent
Wolf et al.

(10) Patent No.: US 9,255,256 B2
(45) Date of Patent: Feb. 9, 2016

(54) EXPRESSION OF FUNCTIONAL CYTOCHOROME P450 MONOOXYGENASE SYSTEM IN ENTEROBACTERIA

(75) Inventors: Charles Roland Wolf, Perth (GB); Thomas Herbert Friedberg, Blairgowrie (GB); Michael Patrick Pritchard, Dundee (GB)

(73) Assignee: BTG INTERNATIONAL LIMITED

( * ) Notice: Subject to any disclaimer, the term of this patent is extended or adjusted under 35 U.S.C. 154(b) by 1063 days.

(21) Appl. No.: 10/369,289

(22) Filed: Feb. 18, 2003

(65) Prior Publication Data

US 2003/0215915 A1    Nov. 20, 2003

Related U.S. Application Data

(62) Division of application No. 09/230,233, filed as application No. PCT/GB97/01917 on Jul. 17, 1997, now Pat. No. 6,566,108.

(30) Foreign Application Priority Data

Jul. 17, 1996  (GB) .................................. 9615032.1

(51) Int. Cl.
    C12N 15/53    (2006.01)
    C12N 9/02     (2006.01)
    C12N 15/52    (2006.01)
    C12P 1/00     (2006.01)

(52) U.S. Cl.
    CPC ............ *C12N 9/0042* (2013.01); *C12N 9/0077* (2013.01); *C12N 15/52* (2013.01); *C12P 1/00* (2013.01); *C07K 2319/02* (2013.01)

(58) Field of Classification Search
    USPC .................. 435/189, 320.1, 252.33; 424/94.2
    See application file for complete search history.

(56) References Cited

U.S. PATENT DOCUMENTS

| 5,240,831 A | 8/1993 | Barnes |
| 5,420,027 A | 5/1995 | Fisher et al. |
| 5,886,157 A | 3/1999 | Guengerich et al. |

FOREIGN PATENT DOCUMENTS

| JP | 61005783 | 0/1986 |
| WO | 89/10963 | 11/1989 |
| WO | 92/10376 | 8/1992 |
| WO | 94/01568 | 1/1994 |

OTHER PUBLICATIONS

Larson J. R. et al. 1991, Alcohol-inducible Cytochrome-450IIE1 Lacking Hydrofobic NH2-terminal Segment Retains catalytic activity and is Membrane-bound When Expressed in *Escherichia coli*, J. Biol. Chem. 266, 7321-7324.*

Hewson R. et al. 1993, The expression of bovine microsomal b5 in *Escherichia coli* and study of the solution and stability of variant proteins, Protein Eng. 6, 953-964.*
Josephy P. D. et al. 1995, Bioactivation of Aromatic Amines by Recombinant Human Cytochrome P4501A2 Expressed in Ames Tester Strain Bacteria: A Substitute for Activation by Mammalian Tissue Preparations, Cancer Res. 55, 799-802.*
Vergeres G. et al. 1995, The Carboxyl terminus of the Mambrane-binding Domain of Cytochrome b5 Spans the Bilayer of the Endoplasmic Reticulum, J. Biol. Chem. 270, 3414-3422.*
Paine M. J. et al. Functional High Level Expression of Cytochrome P450 CYP2D6 Using BAculoviral Expression Systems, Achives of Biochemistry and Biophysics, 1996, 328, 143-150.*
K. Ahn et al. "The Amino-Terminal 29 Amino Acids of Cytochrome P450 2C1 Are Sufficient for Retention in the Endoplasmic Reticulum", J. Biol. Chem. 268(25): 18726-18733 (Sep. 1993).*
Y. Okada et al. "Studies on the Biosynthesis of Microsomal Membrane Proteins", Eur. J. Biochem. 122: 393-402 (1982).*
P. Owen et al. "Molecular Structure of Membrane Vesicles From *Escherichia coli*", PNAS 75(7): 3148-3152. (Jul. 1978).*
Andersen, John F. et al., "Expression of House Fly CYP6A1 and NADPH-Cytochrome P450 Reductase in *Escherichia coli* and Reconstitution of an Insecticide-Metabolizing P450 System," Biochemistry, 33, pp. 2171-2177 (1994).
Andersen, John F. et al., "Substrate Specificity for the Epoxidation of Terpenoids and Active Site Topology of House Fly Cytochrome P450 6A1," Chem. Res. Toxicol., 10, pp. 156-164 (1997).
Aoyama et al., "Estradiol Oxidation by Human P450," Endocrinology, 126, pp. 3103.3106 (1990).
Aoyama, Toshifumi et al., "Five of 12 Forms of Vaccinia Virus-Expressed Human Hepatic Cytochrome P450 Metabolically Activate Aflatoxin $B_1$," Proc. Natl. Acad. Sci. USA, 87, pp. 4790-4793 (1990).
Axen, Eva et al.. "Liver Mitochondria! Cytochrome P450 CYP27 and Recombinant-Expressed Human CYP27 Catalyze 1α-Hydroxylation of 25-Hydroxyvitamin $D_3$," Proc. Natl. Acad. Sci., USA, vol. 91, pp. 10014-10018, Oct. (1994).
Barnes, H.J. et al., "Evaluation of Various Expression Systems for the Synthesis of Cytochrome P-45017α" J. Cell. Biol., 107 (196A) (1998) Abstract No. 1118 (1990).
Barnes, Henry J. et al., "Expression and Enzymatic Activity of Recombinant Cytochrome P450 17 α-Hydroxylase in *Escherichia coli*," Proc. Natl. Acad. Sci. USA, 88, pp. 5597-5601 (1991).

(Continued)

*Primary Examiner* — Rebecca Prouty
(74) *Attorney, Agent, or Firm* — Kilpatrick Townsend & Stockton LLP

(57) ABSTRACT

A bacterial cell containing a functional cytochrome P450 monooxygenase system, said cell comprising a genetic construct capable of expressing a cytochrome P450 and a genetic construct capable of expressing, separately from said cytochrome P450, a cytochrome P450 reductase wherein the N-terminus of the cytochrome P450 and the N-terminus of the cytochrome P450 reductase are each adapted to allow functional coupling of said cytochrome P450 and said cytochrome P450 reductase within said cell. A bacterial cell containing a cytochrome P450 comprising a genetic construct encoding, and capable of expressing, said cytochrome P450 wherein the cytochrome P450 comprises an N-terminal portion which directs the cytochrome P450 to a cellular compartment of membrane of the bacterial cell. The bacterial cells are useful as, for example, bioreactors, in drug testing and mutagenicity testing and as a source of cytochrome P450.

17 Claims, 18 Drawing Sheets

(56) References Cited

OTHER PUBLICATIONS

Figure 1:
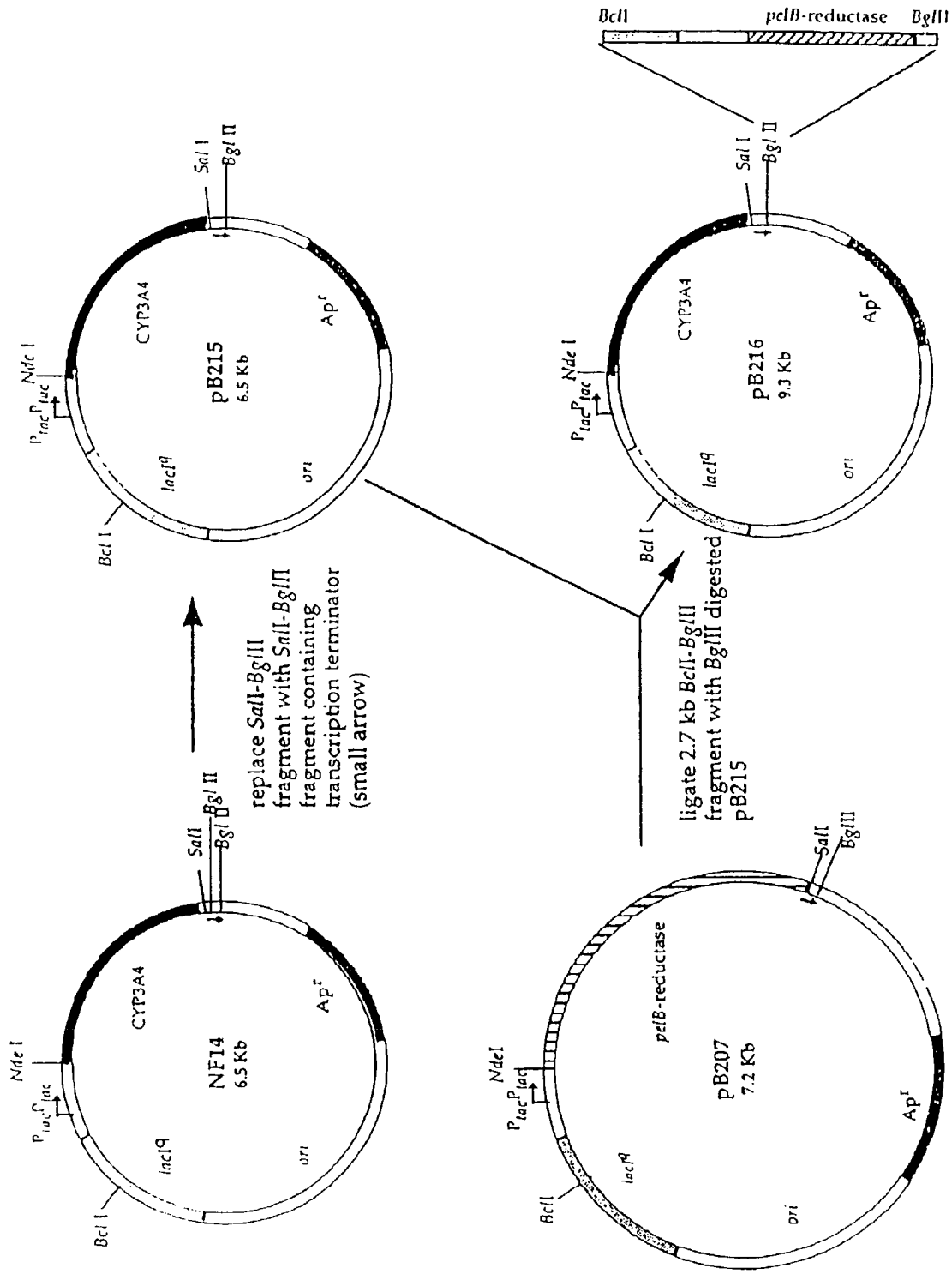

Barnes, Henry J., "Maximizing Expression of Eukaryotic Cytochrome P450s in *Escherichia coil*," Methods in Enzymology, vol. 272, pp. 3-15 (1996).

Barnes, H.J. et al., Proceedings of the 8th International Symposium on Microsomes and Drug Oxidations, Stockholm, Karolinska Institutet, Jun. 25-29 (1990).

Blake, Jennifer A.R. et al., "Coexpression of a Human P450 (CYP3A4) and P450 Reductase Generates a Highly Functional Monooxygenase System in *Escherichia coil*," FEBS Letters 397, pp. 210-214 (1996).

Born, Stephanie L. et al., "*Escherichia Coli* Expression and Substrate Specificities of Canine Cytochrome P450 3A12 and Rabbit Cytochrome P450 3A6," The Journal of Pharmacology and Experimental Therapeutics, vol. 278, No. 2, pp. 957-963 (1996).

Broome-Smith JK et al., "Cleavable Signal Peptides are Rarely Found in Bacterial Cytoplasmic Membrane Proteins (review)," Mol. Membr. Biol., Jan.-Mar.; 11(1):3-8 (1994).

Brown. T.A., "Gene Cloning an Introduction," Chapman & Hall (Publishers) Ltd., Third Edition, pp. 262-268 (1995).

Chen, Ci-Di et al., "Efficient Assembly of Functional Cytochrome P450 2C2 Requires a Spacer Sequence Between the N-Terminal Signal Anchor and Catalytic Domains," The Journal of Biological Chemistry, vol. 272, No. 36, Issue of Sep. 5, pp. 22891-22897 (1997).

Chen, Gia-Fen T. et al., "Suppression of the Negative Effect of Minor Arginine Codons on Gene Expression; Preferential Usage of Minor Codons Within the First 25 Codons of the *Escherichia coil* Genes," Nucleic Acids Research, vol. 18, No. 6, pp. 1465-1473 (1990).

Chun, Young-Jin et al., "Characterization of a Fusion Protein Between Human Cytochrome P450 1A1 and Rat NADPH-P450 Oxidoreductase in *Escherichia coli*," Biochemical and Biophysical Research Communications, 230, pp. 211-214, Article No. RC965918 (1997).

Chun, Young-Jin et al., "Construction of a Human Cytochrome P450 1A1:Rat NADPH—Cytochrome P450 Reductase Fusion Protein cDNA and Expression in *Escherichia coli*, Purification, and Catalytic Properties of the Enzyme in Bacterial Cells and after Purification," Archives of Biochemistry and Biophysics, vol. 330, No. 1, Jun. 1. pp. 48-58, Article No. 0224 (1996).

Crespi, Charles L. et al., "The Development of a Human Cell Line Stably Expressing Human CYP3A4: Role in the Metabolic Activation of Aflatoxin B, and Comparison to CYP1A2 and CYP2A3," Carcinogenesis, 12, pp. 355-359 (1991).

Dehal, Shangara S. et al., "CYP2D6 Catalyzes Tamoxifen 4-Hydroxylation in Human Liver", Cancer Research, pp. 3402-3406, Aug. 15 (1997).

Doehmer, Johannes et al., "Stable Expression of Rat Cytochrome P-450IIB1 cDNA in Chinese Hamster Cells (V79) and Metabolic Activation of Aflatoxin $B_1$," Proc. Natl. Acad. Sci. USA, vol. 85, pp. 5769-5773, Aug. (1988).

Dong, Jinsheng, "Coexpression of Mammalian Cytochrome P450 and Reductase in *Escherichia coli*," Archives of Biochemistry and Biophysics, vol. 327, No. 2, Mar. 15, pp. 254-259, Article No. 0118 (1996).

Dong, Mi-Sook et al., "Recombinant Human Cytochrome P450 1A2 and an N-Terminal-Truncated Form: Construction, Purification, Aggregation Properties, and Interactions with Flavodoxin, Ferredoxin, and Nadph-Cytochrome P450 Reductase," Archives of Biochemistry and Biophysics, vol. 327, No. 1, Mar. 1, pp. 11-19, Article No. 0086 (1996).

Erdmann, Bettina et al., "Immunocytochemical Localization of Heterologously Expressed Adrenodoxin and its Electron Acceptor Cytochrome P4501181 in *Escherichia coli*," European Journal of Cell Biology, 65, pp. 220-228 (1994).

Estabrook, Ronald W. et al., "Cytochrome P-450s as Toxicogenic Catalysts: The Influence of Dehydroepiandrosterone," Xenobiotics and Cancer, pp. 33-44 (1991).

Fang, Xiaojun et al., "Stoichiometry of 7-Ethoxycoumarin Metabolism by Cytochrome P450 2B1 Wild-Type and Five Active-Site Mutants", FEBS Letters 416, pp. 77-80 (1997).

Fisher, Charles W. et al., "Construction of Plasmids and Expression in *Escherichia coli* of Enzymatically Active Fusion Proteins Containing the Heme-Domain of a P450 Linked to NADPH-P450 Reductase", Methods in Enzymology, vol. 272, pp. 15-25 (1996).

Fisher, Charles W. et al., "High-Level Expression in *Escherichia coli* of Enzymatically Active Fusion Proteins Containing the Domains of Mammalian Cytochromes P450 and Nadph-P450 Reductase Flavoprotein," Proc. Natl. Acad. Sci. USA, vol. 89, pp. 10817-10821, Nov. (1992).

Fisher, Charles W. et al., "High-Level Expression of Functional Human Cytochrome P450 1A2 in *Escherichia coli*," Expression of Recombinant Human, The FASEB Journal, vol. 6, Jan., pp. 759-764 (1992).

Gillam, Elizabeth M.J. et al., "Expression of Cytochrome P450 2D6 in *Escherichia coli*, Purification, and Spectral and Catalytic Characterization," Arch. Biochem. Biophys., vol. 319, No. 2, Jun. 1, pp. 540-550 (1995).

Gillam, Elizabeth M.J. et al., "Expression of Cytochrome P450 3A5 in *Escherichia coli* :Effects of 5' Modification Purification, Spectral Characterization, Reconstitution Conditions, and Catalytic Activities," Arch. Biochem. Biophys. vol. 317, No. 2, Mar. 10, pp. 374-384 (1995). (Missing pp. 380-381.)

Gillam, E.M.J. et al., "Expression of Human Cytochrome P-450 3A4 and 2E1 in the Bacterium *Escherichia Coli*," Faseb Journal, 6, A323-A323 (Abstract) (1992).

Gillam, Elizabeth M.J. et al., "Expression of Modified Human Cytochrome P450 2E1 in *Escherichia coli*, Purification, and Spectral and Catalytic Properties," Arch. Biochem. Biophys., vol. 312, No. 1, pp. 59-66 (1994).

Gillam, Elizabeth M. J. et al., "Expression of Modified Human Cytochrome P450 3A4 in *Escherichia coli* and Purification and Reconstitution of the Enzyme," Archives of Biochemistry and. Biophysics, vol. 305. No. 1, Aug. 15, pp. 123-131 (1993).

Gillam, E.M.J. et al., "Expression of P450 3A7 in *Escherichia Coli*: Effects of 5' Modification and Catalytic Characterization of the Recombinant Enzyme," Faseb Journal, 11, P144 (Abstract) (1997).

Gonzalez, Frank J. et al., "Cytochromes P450 Expression Systems," Annu. Rev. Pharmacol. Toxicol., 35, pp. 369-390 (1995).

Guengerich, F. Peter, "Comparisons of Catalytic Selectivity of Cytochrome P450 Subfamily Enzymes from Different Species," Chemico-Biological Interactions 106, pp. 161-182 (1997).

Guengerich, F. Peter et al., "Expression of Human Cytochrome P450 Enzymes in Yeast and Bacteria and Relevance to Studies on Catalytic Specificity," Toxicology 82, pp. 21-37 (1993).

Guengerich, F. Peter et al., "Heterologous Expression of Human Drug-Metabolizing Enzymes," Drug Metabolism and Disposition, vol. 25, pp. 1234-1241 (1997).

Guengerich, F. Peter et al., "New Applications of Bacterial Systems to Problems in Toxicology," Clinical Reviews in Toxicology, 26(5):551-583 (1996).

Guengerich, F. Peter et al., "Kinetics of Ferric Cytochrome P450 Reduction by NADPH-Cytochrome P450 Reductase: Rapid Reduction in the Absence of Substrate and Variations Among Cytochrome P450 Systems," Biochemistry, 36, pp. 14741-14750 (1997).

Guo, Zuyu et al., "Expression of Modified Human Cytochrome P450 1A1 in *Escherichia coli*: Effects of 5' Substitution, Stabilization, Purification, Spectral Characterization and Catalytic Properties," Arch. Biochem. Biophys., vol. 312, No. 2, Aug. 1, pp. 436-446 (1994).

Halkier, Barbara Ann et al., "Purification and Characterization of Recombinant Cytochrome $P450_{TYR}$ Expressed at High Levels in *Escherichia coli*," Archives of Biochemistry and Biophysics, vol. 322, No. 2, Oct. 1, pp. 369-377 (1995).

Halpert, James R. et al., "Engineering of Cytochrome P450 2B1 Specificity, Conversion of an Adrogen 16β Hydroxylase to a 15α Hydroxylase," The Journal of Biological Chemistry, vol. 268, No. 6, Issue of Feb. 25, pp. 4453-4457 (1993).

Hammons, George J. et al., "Metabolism of Carcinogenic Heterocyclic and Aromatic Amines by Recombinant Human Cytochrome P450 Enzymes," Carcinogenesis, vol. 18, No. 14, pp. 851-854 (1997).

Harlow, Greg R. et al., "Mutagenesis Study of Asp-290 in Cytochrome P450 2811 Using a Fusion Protein with Rat NADPH-

(56) References Cited

OTHER PUBLICATIONS

Cytochrome P450 Reductase," Archives of Biochemistry and Biophysics, vol. 326, No. 1, Feb. 1, pp. 85-92, Article No. 0050 (1996).
He, You Qun et al., "*Escherichia coli* Expression of Site-Directed Mutants of Cytochrome P450 2B1 From Six Substrate Recognition Sites: Substrate Specificity and Inhibitor Selectivity Studies," Chem. Res. Toxicol., 8, pp. 574-579 (1995).
Holmans, Priscilla L. et al., "The High-Level Expression in *Escherichia coli* of the Membrane-Bound Form of Human and Rat Cytochrome $b_5$ and Studies on Their Mechanism of Function," Archives of Biochemistry and Biophysics, vol. 312, No. 2, Aug. 1, pp. 554-565 (1994).
Hotze, Michael et al., "Cinnamate 4-Hydroxylase from *Catharanthus roseus*, and a Strategy for the Functional Expression of Plant Cytochrome $P_{450}$ Proteins as Translational Fusions with $P_{450}$ Reductase in *Escherichia coli*," FEBS Letters 374, pp. 345-350 (1995).
Hsu, Li-Chung et al., "The N-Terminal Hydrophobic Domain of P450c21 is Required for Membrane Insertion and Enzyme Stability," The Journal of Biological Chemistry, vol. 268, No. 20, Issue of Jul. 15, pp. 14682-14686 (1993).
Hu, Meng-Chun et al., "Expression of Human 21-Hydroxylase (P450c21) in Bacterial and Mammalian Cells: A System to Characterize Normal and Mutant Enzymes," Molecular Endocrinology, vol. 4, No. 6, pp. 893-898 (1990).
Imai, Tsuneo et al., "Expression and Purification of Functional Human 17α-Hydroxylase/17,20-Lyase (P450c17) in *Escherichia coli*," The Journal of Biological Chemistry, vol. 268, No. 26, Issue of Sep. 15, pp. 19681-19689 (1993).
Izard, Jennifer W. et al., "Signal Peptides: Exquisitely Designed Transport Promoters," Molecular Microbiology 13(5), pp. 765-773 (1994).
John, Gilbert H. et al., "*Escherichia coli* Expression and Characterization of Cytochromes P450 2B11, 2B1, and 2B5," Archives of Biochemistry and Biophysics, vol. 314, No. 2, Nov. 1, pp. 367-375 (1994).
Josephy, P. David et al., "Bioactivation of Aromatic Amines by Recombinant Human Cytochrome P4501A2 Expressed Ames Tester Strain Bacteria: A Substitute for Activation by Mammalian Tissue Preparations," Cancer Res., 55, pp. 799-802 (1995).
Kawashima, Hidenori et al., "Protein Expression, Characterization, and Regulation of CYP4F4 and CYP4F5 Cloned from Rat Brain," Archives of Biochemistry and Biophysics, vol. 347, No. 1, Nov. 1, pp. 148-154, Article No. BB970342 (1997).
Kempf, Andreas C. et al.. "Truncated Human P450 2D6: *Expression in Escherichia coli*, $Ni^{2+}$-Chelate Affinity Purification, and Characterization of Solubility and Aggregation," Archives of Biochemistry and Biophysics, vol. 321, No. 2, Aug. 20, pp. 277-288 (1995).
Larson, Jane R. et al., "Alcohol-Inducible Cytochrome P-450IIE1 Lacking the Hydrophobic $NH_2$-terminal Segment Retains Catalytic Activity and Is Membrane-bound When Expressed in *Escherichia coli*," J. Biol. Chem., 266, pp. 7321-7324 and Faseb Journal, 5, A1515 (Abstract 6638) (1991).
Li, Yan Chun et al., "The Expression of a Catalytically Active Cholesterol 7α-Hydroxylase Cytochrome P450 in *Escherichia coli*," The Journal of Biological Chemistry, vol. 266, No. 29, Issue of Oct. 15, pp. 19186-19191 (1991).
Looman, A.C. et al., "Influence of the codon following the AUG initiation codon on the expression of a modified lacZ gene in *Escherichia coli*," The EMBO Journal, vol. 6, No. 8, pp. 2489-2492(1987).
Nebert, Daniel W. et al., "The P450 Superfamily: Updated Listing of All Genes and Recommended Nomenclature for the Chromosomal Loci," DNA, vol. 8, No. 1, pp. 1-13 (1989).
Nelson, David R. et al., "P450 Superfamily Update on New Sequences, Gene Mapping, Accession Nos. And Nomenclature," Pharmacogenetics, 6, pp. 1-42 (1996).
Nishimoto, Masazumi et al., "Cytochrome P450 4A4: Expression in *Escherichia coli*, Purification, and Characterization of Catalytic Properties," Biochemistry, 32, pp. 8863-8870 (1993).

Parikh, Asit et al., "Drug Metabolism by *Escherichia coli* Expressing Human Cytochromes P450," Nature Biotechnology, vol. 15, Aug., pp. 784-788 (1997).
Parikh, Asit et al., "Expression, Purification, and Characterization of a Catalytically Active Human Cytochrome P450 1A2:Rat NADPH-Cytochrome P450 Reductase Fusion Protein," Protein Expression and Purification, 9, pp. 346-354 (1997).
Parikh, Asit et al., "In Vivo Catalysis by Constructs Co-Expressing Human P450s and NADPH-P450 Reductase in *Escherichia coli*," Faseb Journal, 11, P120 (Abstract) (1997).
Peng, Hwei-Ming et al., "Isolation and Heterologous Expression of Cloned cDNAs for Two Rabbit Nasal Microsomal Proteins, CYP2A10 and CYP2A11, That Are Related to Nasal Microsomal Cytochrome P450 Form a," The Journal of Biological Chemistry, vol. 268, No. 23, Issue of Aug. 15, pp. 17253-17260 (1993).
Pernecky, S.J. et al., "Characterization of Truncated Rabbit P450 ISO-Forms Expressed in the Membrane and Cytosol of *Escherichia coli*," Faseb Journal, 6, A323-A323 (Abstract) (1992).
Pernecky, Steven J. et al., "Expression of Truncated Forms of Liver Microsomal P450 Cytochromes 2B4 and 2E1 in *Escherichia coli*: Influence of $NH_2$-terminal Region on Localization in Cytosol and Membranes," Proc. Natl. Acad. Sci., USA, vol. 90, pp. 2651-2655, Apr. (1993).
Pernecky, Steven J. et al., "Subcellular Localization, Aggregation State, and Catalytic Activity of Microsomal P450 Cytochromes Modified in the $NH_2$-Terminal Region and Expressed in *Escherichia coil*," Archives of Biochemistry and Biophysics, vol. 318, No. 2, Apr. 20, pp. 446-456 (1995).
Porter, T.D. et al., "Expression of Cytochrome P-450 in Yeast and *Escherichia Coli*," Proceedings of the $8^{th}$ International Symposium on Microsomes and Drug Oxidations, Stockholm, Karolinska Institutet, Jun. 25-29 (Abstract) (1990).
Porter, Todd D. et al., "Expression of Mammalian P450s in *Escherichia coli*," Methods in Enzymology, vol. 206, pp. 108- 116 (1991).
Porter, Todd D., "Mutagenesis at a Highly Conserved Phenylalanine in Cytochrome P450 2E1 Affects Heme Incorporation and Catalytic Activity", Biochemistry, 33, 5942-5946 (1994).
Pritchard, Micheal P. et al., "A General Strategy for the Expression of Recombinant Human Cytochrome P450s in *Escherichia coli* Using Bacterial Signal Peptides: Expression of CYP3A4, CYUP2A6, and CYP2E1," Archives of Biochemistry and Biophysics, vol. 345, No. 2, Sep. 15, pp. 342-354 (1997).
Renaud, J.P. et al., "Recombinant Yeast in Drug Metabolism," Toxicology, 82, pp. 39-52 (1993).
Richardson, Toby H. et al., "A Universal Approach to the Expression of Human and Rabbit Cytochrome P450s of the 2C Subfamily in *Escherichia coli*," Archives of Biochemistry and Biophysics, vol. 323, No. 1, Oct. 20, pp. 87-96 (1995).
Richardson, T.H. et al., "Expression and Characterization of Human Cytochrome P450 2C Enzymes in *E. Coli* Identification of P450 2C19 as a Progesterone 21-Hydroxylase", Faseb Journal, 9, A1489-A1489 (Abstract) (1995).
Richardson, T.H. et al., "Isolation and Characterization of Recombinant P450 2C3 Expressed in *E. Coli*," Faseb Journal, 6, A1202-A1202 (Abstract) (1992).
Richardson, T.H. et al., "Purification and Characterization of Recombinant-Expressed Cytochrome P450 2C3 from *Escherichia coli*: 2C3 Encodes the 6β-Hydroxylase Deficient Form of P450 3b," Archives of Biochemistry and Biophysics, vol. 300, No. 1, Jan., pp. 510-516 (1993).
Roman, L.J. et al., "Expression of P4504A6 Protein in *E. Coli*," Faseb Journal, 7, A264-A264 (Abstract) (1993).
Roman, L.J. et al., "Expression of P4504A6 Protein in *E. Coli*," Faseb Journal, 7, A1199-A1199 (Abstract) (1993).
Sagara, Yasuhiro et al., "Expression in *Escherichia coli* of Functional Cytochrome $P450_{C17}$ Lacking its Hydrophobic Amino-Terminal Signal Anchor," Archives of Biochemistry and Biophysics, vol. 304, No. 1, Jul., pp. 272-278 (1993).
Sandhu, Punam et al., "Expression of Modified Cytochrome P450 2C10 (2C9) in *Escherichia coil*, Purification, and Reconstitution of Catalytic Activity," Archives of Biochemistry and Biophysics, vol. 306, No. 2, Nov. 1, pp. 443-450 (1993).

(56) References Cited

OTHER PUBLICATIONS

7-Purification, Sandhu, Punam et al., "Expression of Modified Human Cytochrome P450 1A2 in *Escherichia coli*: Stabilization, Spectral Characterization, and Catalytic Activities of the Enzyme," Archives of Biochemistry and Biophysics, vol. 309, No. 1, Feb. 15, pp. 168-177 (1994).

Savas, Uzen et al., "Biological Oxidations and P450 Reactions," Archives of Biochemistry and Biophysics, vol. 347, No. 2, Nov. 15, pp. 181-192 (1997).

Shen, Anna L. et al., "Structural Analysis of the FMN Binding Domain of NADPH-Cytochrome P-450 Oxidoreductase by Site-directed Mutagenesis," The Journal of Biological Chemistry, vol. 264, No. 13, May 5, pp. 7584-7589 (1989).

Shet, Manjunath S. et al., "Human Cytochrome P450 3A4: Enzymatic Properties of a Purified Recombinant Fusion Protein Containing NADPH-P450 Reductase," Proc. Natl. Acad. Sci. USA, vol. 90, pp. 11748-11752, Dec. (1993).

Shet, Manjunath S. et al., "Purification and Enzymatic Properties of a Recombinant Fusion Protein Expressed in *Escherichia coli* Containing the Domains of Bovine P450 17A and Rat NADPH-P450 Reductase," Archives of Biochemistry and Biophysics, vol. 311, No. 2, Jun., pp. 402-417 (1994).

Shet, Manjunath S. et al., "The Effects of Cytochrome $b_5$, NADPH-P450 Reductase, and Lipid on the Rate of 6β-Hydroxylation of Testosterone as Catalyzed by a Human P450 3A4 Fusion Protein," Arch. Of Biochem. And Biophysics, vol. 318, No. 2, pp. 314-321 (1995).

Shet, Manjunath S. et al., "The Function of Recombinant Cytochrome P450s in Intact *Escherichia coli* Cells: The 17α-Hydroxylation of Progesterone and Pregnenolone by P450c17," Archives of Biochemistry and Biophysics, vol. 339, No. 1, Mar. 1, pp. 218-225 (1997).

Shet, Manjunath S. et al., "The Omega-Hydroxylation of Lauric Acid: Oxidation of 12-Hydroxylauric Acid to Dodecanedioic Acid by a Purified Recombinant Fusion Protein Containing P450 4A1 and NADPH-P450 Reductase," Archives of Biochemistry and Biophysics, vol. 330, No. 1, Jun. 1, pp. 199-208 (1996).

Shimada, Tsutomu et al., "Activation of Procarcinogens by Human Cytochrome P450 Enzymes Expressed in *Escherichia coli*. Simplified Bacterial Systems for Genotoxicity Assays," Carcinogenesis, 15, pp. 2523-2529 (1994).

Shimada, Tsutomu et al., "Oxidation of Xenobiotics by Recombinant Human Cytochrome P450 1B1," Drug Metabolism and Distribution, vol. 29, No. 5, pp. 617-622 (1997).

Smith, Graeme C.M. et al., "Dissection of NADPH-Cytochrome P450 Oxidoreductase into Distinct Functional Domains," Proc. Natl. Acad. Sci., vol. 91, pp. 8710-8714, Aug. (1994).

Smith, Theresa J. et al., "Metabolism of 4-(methylnitrosamino)-1-(3-pyridyl)-1-butanone (NNK) by Human Cytochrome P450 1A2 and its Inhibition by Phenethyl Isothiocyanate," Carcinogenesis, vol. 17, No. 4, pp. 809-813 (1996).

Strobel, Sharon M. et al., "Reassessment of Cytochrome P450 2B2: Catalytic Specificity and Identification of Four Active Site Residues," Biochemistry, 36, pp. 11697-11706 (1997).

Swart, P. et al., "The Catalytic Activity of Human and Bovine Adrenal Cytochromes P-450 $_{17\alpha,lyase}$ Expressed in COS 1 Cells," J. Cell. Biol., 107 (196A), Abstract 1120 (1988).

Von Wachenfeldt, Claes et al., "Microsomal P450 2C3 is Expressed as a Soluble Dimer in *Escherichia coli* Following Modifications of its N-Terminus," Archives of Biochemistry and Biophysics, vol. 339, No. 1, Mar. 1, pp. 107.114, Article No. BB969859 (1997).

Wada, Akira et al., "Expression of Functional Bovine Cholesterol Side Chain Cleavage Cytochrome P450 (P450scc) in *Escherichia coli*," Archives of Biochemistry and Biophysics, vol. 290, No. 2, Nov. 1, pp. 376-380 (1991).

Wang, Huamin et al., "Regulation of CYP3A9 Gene Expression by Estrogen and Catalytic Studies Using Cytochrome P450 3A9 Expressed in *Escherichia coli*," Archives of Biochemistry and Biophysics, vol. 344, No. 2, Aug. 15, pp. 365-372 (1997).

Waterman, M.R. et al., "Expression of P-450 Enzyme Activities in Heterologous Cells by Transfection," Arch. Toxicol., Suppl. 13, pp. 155-163 (1989).

Waterman, Michael R., "Heterologous Expression of Cytochrome P-450 in *Escherichia coli*," Biochemical Society Transactions, P-450 Biotechnology, pp. 1081-1085 (1993).

Waterman, Michael R., "Heterologous Expression of Mammalian P450 Enzymes," Advances in Enzymology and Related Areas of Molecular Biology, vol. 68, pp. 37-66 (1994).

White, Perrin C. et al., "Cloning and Expression of cDNA Encoding a Bovine Adrenal Cytochrome P450 Specific for Steroid 21-Hydroxylation (P-450$_{C21}$)," Annals New York Academy of Sciences, 435, pp. 229-230 (1984).

Winters, Debra K. et al., "Expression of a Catalytically active human cytochrome P-4502E1 in *Escherichia coli*," Biochimica at Biophysica Acta, 1156, pp. 43-49 (1992).

Yabusaki, Y., "Artificial P450/Reductase Fusion Enzymes: What Can We Learn From Their Structures?," Biochimie, 77, pp. 594-603 (1995).

Yamazaki, Hiroshi et al., "Lack of Electron Transfer from Cytochrome $b_5$ in Stimulation of Catalytic Activities of Cytochrome P450 3A4," The Journal of Biological Chemistry, vol. 271, No. 44, Issue of Nov. 1, pp. 27438-27444 (1996).

Yamazaki, Hiroshi et al., "Procarcinogen Activation by Cytochrome P450 3A4 and 3A5 Expressed in *Escherichia coli* and by Human Liver Microsomes," Carcinogenesis, vol. 16, No. 9, pp. 2167-2170 (1995).

Yamazaki, Hiroshi et al., "Reconstitution of Recombinant Cytochrome P450 2C10(2C9) and Comparison with Cytochrome P450 3A4 and Other Forms: Effects of Cytochrome P450-P450 and Cytochrome P450-$b_5$ Interactions," Archives of Biochemistry and Biophysics, vol. 342, No. 2, Jun. 15, pp. 329-337 (1997).

\* cited by examiner

|  | 1 | 2 | 3 | 4 | 5 |
|---|---|---|---|---|---|
| Activity | 6 | 47 | 18 | 1153 | 159 |

A. *pelB*-CYP3A4

B. *ompA*-CYP3A4

| CONSTRUCT | | EXPRESSION LEVEL (nmol/l culture) | | CYP3A4 CONTENT OF MEMBRANES (nmol/mg protein) |
|---|---|---|---|---|
| | | WHOLE CELLS | MEMBRANES | |
| pelB-CYP3A4 | control | 95 ± 23 (4) | 31 ± 6 (4) | 0.11 ± 0.01 (4) |
| | + δ-ALA | 143 ± 47 (3) | 51 ± 5 (3) | 0.18 ± 0.01 (3) |
| ompA-CYP3A4 | control | 504 ± 62 (3) | 236 ± 29 (3) | 0.70 ± 0.06 (3) |
| | + δ-ALA | 502 ± 98 (3) | 278 ± 44 (3) | 0.87 ± 0.07 (3) |

Figure 7

A. CYP2D6 expressed alone

B. CYP2D6 co-expressed with reductase

| CONSTRUCT | | EXPRESSION LEVEL (nmol/l culture) | | CYP2D6 CONTENT OF MEMBRANES (nmol/mg protein) |
|---|---|---|---|---|
| | | WHOLE CELLS | MEMBRANES | |
| 2D6 alone | control | 211 ± 63 (3) | 68 ± 16 (3) | 0.26 ± 0.06 (3) |
| | + δ-ALA | 481 ± 58 (3) | 133 ± 31 (3) | 0.49 ± 0.10 (3) |
| 2D6 + reductase | control | 138; 163 (2) | 29; 22 (2) | 0.138; 0.065 (2) |
| | + δ-ALA | 365 ± 73 (3) | 51 ± 8 (3) | 0.21 ± 0.04 (3) |

Figure 10

| Isozyme | P450 Cellular Yield (nmoles / l) | Reference |
|---|---|---|
| CYP3A4 (NF14) | 300 | (16) |
| ompA-CYP3A4 | 500 | LINK, 96 |
| | | |
| CYP2D6 | 100 | (35) |
| ompA-CYP2D6 | 480 | LINK, 96 |

Figure 12

WHOLE CELLS  MEMBRANES

| CONSTRUCT | EXPRESSION LEVEL (nmol/l culture) | | CYP2A6 CONTENT OF MEMBRANES (nmol/mg protein) |
|---|---|---|---|
| | WHOLE CELLS | MEMBRANES | |
| ompA-2A6 | 193 ± 21 | 72 ± 15 | 0.28 ± 0.05 |

Figure 14

EXPRESSION OF FUNCTIONAL CYTOCHOROME P450 MONOOXYGENASE SYSTEM IN ENTEROBACTERIA

This application is a division of U.S. patent application Ser. No. 09/230,233 filed May 17, 1999, now U.S. Pat. No. 6,566,108, which is a national phase application of PCT/GB97/01917 filed Jul. 17, 1997, and claims priority to British patent application 9615032.1 filed Jul. 17, 1996.

The present invention relates to the expression of cytochrome P450 in bacteria; in particular the invention relates to the expression of an active eukaryotic cytochrome P450 enzyme system in bacteria, particularly Enterobacteria.

BACKGROUND AND PRIOR ART

Cytochrome P450 monooxygenases (P450s) form a superfamily of haemoproteins which catalyse the metabolism of a wide range of compounds. They catalyse the oxidation of lipophilic chemicals through the insertion of one atom of molecular oxygen into the substrate (Porter & Coon (1991) *J. Biol. Chem.* 261, 13469-13472). Mammalian P450s catalyse the metabolism of endogenous and exogenous compounds, including steroids, therapeutic drugs and carcinogens (Guengerich (1987) in *"Enzymology of rat liver cytochromes P450"*, ed. Guengerich, F. P., CRC Press, Boca Raton Fla., Vol. 1, pp 1-54; Guengerich & Shimada (1991) *Chem. Res. Toxicol.* 4, 391-407; Gonzalez (1992) *Trends in Pharmacol. Sci.* 12, 346-352). The different mammalian P450s exhibit a unique but overlapping substrate specificity and display a high regio- and stereoselectivity (Crespi et al (1993) *Toxicology* 82, 89-104). Based on their major functions, mammalian P450s can be subdivided into two major classes: those involved primarily in the metabolism of steroids and bile acids, and those which mainly metabolise xenobiotics. The xenobiotic-metabolising P450s are typically located in the endoplasmic reticulum of certain mammalian cells such as liver cells and are termed microsomal P450s.

The compounds metabolised by the latter group of P450s include therapeutic drugs such as cyclosporin, nifedipine and debrisoquine as well as carcinogens such as polycyclic aromatic hydrocarbons, nitrosamines and arylamines. To be catalytically active, microsomal P450s require a supply of electrons which are shuttled from NADPH via the FMN and FAD prosthetic groups of NADPH-cytochrome P450 oxidoreductase (P450 reductase; EC 1.6.2.4) (Smith et al (1994) *Proc. Natl. Acad. Sci. USA* 91, 8710-8714).

Comparison of the primary structures of P450s indicates that they are structurally related to each other and are most likely derived from a common ancestor. Based on their primary structure the P450s are classified into families such as CYP1, CYP2 etc (Nelson et al (1996) *Pharmacogenetics* 6, 1-42).

Because of the importance of mammalian P450s in the metabolism of therapeutic compounds and carcinogens, attempts have been made to express mammalian P450s in heterologous systems. For example, mammalian cells have been used to express P450s heterologously as described by Doehmer et al (1988) *Proc. Natl. Acad. Sci. USA* 85, 5769-5773; Aoyama et al (1990) *Proc. Natl. Acad. Sci. USA* 87, 4790-4793; and Crespi et al (1991) *Carcinogenesis* 12, 355-359.

Yeast cells have also been used for the heterologous expression of cytochrome P450, for example by Renaud et al (1993) *Toxicology* 82, 39-52 and Bligh et al (1992) *Gene* 110, 33-39.

More recently mammalian P450s have been expressed in *Escherichia coli.*

Gillam et al (1993) *Arch. Biochem. Biophys.* 305, 123-131 describes the expression of modified human cytochrome P450 3A4 in *E. coli* and purification and reconstitution of the enzyme.

Barnes et al (1991) *Proc. Natl. Acad. Sci. USA* 88, 5597-5601 describes the expression and enzymatic activity of recombinant cytochrome P450 17α-hydroxylase in *E. coli.*

Larson et al (1991) *J. Biol. Chem.* 266, 7321-7324 describes that expression of cytochrome P450 IIE1 lacking the hydrophobic $NH_2$-terminal segment retains catalytic activity.

Shimada et al (1994) *Carcinogenesis* 15, 2523-2529 describes the activation of procarcinogens by human cytochrome P450 enzymes expressed in *E. coli.*

Shet et al (1993) *Proc. Natl. Acad. Sci. USA* 90, 11748-11752 describes the enzymatic properties of a purified recombinant fusion protein containing NADPH-P450 reductase.

Shet et al (1995) *Arch. Biochem. Biophys.* 318, 314-321 describes some properties of a recombinant fusion protein containing the haem domain of human P450 3A4 and the flavin domains of rat cytochrome P450 reductase.

Jenkins & Waterman (1994) *J. Biol. Chem.* 269, 27401-27408 describes that flavodoxin and NADPH-flavodoxin reductase from *E. coli* support bovine cytochrome P450 c17 hydroxylase activities.

Fisher et al (1992) *FASEB J.* 6, 759-764 describes the expression of human cytochrome P450 1A2 in *E. coli.*

Fisher et al (1992) *Proc. Natl. Acad. Sci. USA* 89, 10817-10821 describes the expression in *E. coli* of fusion proteins containing the domains of mammalian cytochromes P450 and NADPH-P450 reductase flavoprotein.

Chun & Chiang (1991) *J. Biol. Chem.* 266, 19186-19191 describes the expression of cholesterol 7α-hydroxylase cytochrome P450 in *E. coli.*

Richardson et al (1995) *Arch. Biochem. Biophys.* 323, 87-96 describes the expression of human and rabbit cytochrome P450s of the 2C subfamily in *E. coli.*

Gillam et al (1995) *Arch. Biochem. Biophys.* 319, 540-550 describes the expression of cytochrome P450 2D6 in *E. coli.*

Dong & Porter (1996) *Arch. Biochem. Biophys.* 327, 254-259 describes a study in which P450 reductase containing an N-terminal fusion to an ompA signal peptide is co-expressed in *E. coli* with human P450 2E1 in which the second codon of the P450 (serine) is replaced with an alanine; no other changes to the P450 were made. In vivo activity with whole cells could not be demonstrated.

WO 94/01568 describes the expression of $P450_{17\alpha}$-hydroxylase in *E. coli* and also its fusion to a P450 reductase enzyme domain and expression of the fusion protein in *E. coli.* P450 enzyme hybrids, incorporating the N-terminal nine amino acids from bovine $P450_{17\alpha}$-hydroxylase are also disclosed.

U.S. Pat. No. 5,240,831 describes expression of $P450_{17\alpha}$-hydroxylase in *E. coli* in a biologically active form without the need for co-expression or admixture of a cytochrome P450 reductase.

Gillam et al (1995) *Arch. Biochem. Biophys.* 317, 374-384 describes the expression of cytochrome P450 3A5 in *E. coli.*

Gillam et al (1994) *Arch. Biochem. Biophys.* 312, 59-66, describes the expression of modified human cytochrome P450 2E1 in *E. coli.*

Shet et al (1994) *Arch. Biochem. Biophys.* 311, 402-417 describes a recombinant fusion protein expressed in *E. coli* containing the domains of bovine P450 17A and rat NADPH-P450 reductase.

Josephy et al (1995) *Cancer Res.* 55, 799-802 describes the bioactivation of aromatic amines by recombinant human cytochrome P450 1A2 expressed in *Salmonella typhimurium*.

Despite the extensive efforts to express an effective eukaryotic, particularly mammalian, P450 monooxygenase enzyme system in bacteria to date no system which is capable of metabolising compounds in whole cells has been devised. This is particularly the case for xenobiotic-metabolising P450s which require a P450 reductase for enzymatic activity. More particularly, no bacterial cell system has previously been devised which allows cytochrome P450 and cytochrome P450 reductase to form a functional cytochrome P450 monooxygenase system when expressed separately in the same bacterial cell. Similarly, despite considerable efforts to produce bacteria which express a high level of a eukaryotic xenobiotic-metabolising P450, no satisfactory system has so far been devised.

One object of the invention is to provide superior systems for expressing P450s in a functional form in intact bacterial cells.

A further object of the invention is to provide an improved system for expressing P450s whether or not with P450 reductase.

Bacterial systems which express a functional P450 enzyme system in whole cells are useful as "bioreactors" or they may find uses in drug-testing or carcinogen-testing systems or as biosensors or in environmental remediation or in the production of hormones and so on. The expression of eukaryotic P450s at high levels in bacteria provides a source of P450 for structural studies.

SUMMARY OF INVENTION

A first aspect of the invention provides a bacterial cell containing a functional cytochrome P450 monooxygenase system said cell comprising a genetic construct capable of expressing a cytochrome P450 and a genetic construct capable of expressing, separately from said cytochrome P450, a cytochrome P450 reductase wherein the N-terminus of the cytochrome P450 and the N-terminus of the cytochrome P450 reductase are each adapted to allow functional coupling of said cytochrome P450 and said cytochrome P450 reductase within said cell.

Preferably, the bacterial cell expresses a cytochrome P450 monooxygenase system which has a specific activity of at least 50 pmol/min/mg protein, more preferably at least 250 pmol/min/mg protein and still more preferably at least 500 pmol/min/mg protein. These levels are measured using a suitable and effective substrate for the cytochrome P450 monooxygenase system. Preferably the said preferred specific activities are of whole cells but the activities may also be those found in fractions of the cells such as the membrane fraction.

Thus, a bacterial cell is provided that contains a functional cytochrome P450 monooxygenase system said cell comprising a genetic construct which expresses a cytochrome P450 and a genetic construct which expresses, separately from said cytochrome P450, a cytochrome P450 reductase wherein the said cytochrome P450 and the said cytochrome P450 reductase functionally couple within said cell.

By "cytochrome P450" we include any haem-containing polypeptide which gives an absorption maximum in the region of 450 nm±5 nm in a reduced CO difference spectrum by virtue of the formation of a CO adduct of the Fe(II) of said haem.

It is envisaged that the invention can be practised on any cytochrome P450.

Preferably, the cytochrome P450 is a eukaryotic cytochrome P450; more preferably the cytochrome P450 is a mammalian cytochrome P450 and still more preferably the cytochrome P450 is a human cytochrome P450.

A large number of cytochrome P450 cDNAs or genes have been cloned including a large number of eukaryotic cytochrome P450 cDNA, particularly mammalian cytochrome P450 cDNAs. For example, Nelson et al. (1996) *Pharmacogenetics* 6, 1-42, incorporated herein by reference, lists the known cytochrome P450 cDNA and genes and groups them into gene families and subfamilies based on the degree of sequence similarity and, to some extent, their chromosomal localization. Details of cytochrome P450 sequences are also available on the Internet.

These cytochrome P450 cDNAs and genes can readily be obtained using cloning methods well known in the art, some of which are described below and for example, described in Sambrook et al (1989) Molecular Cloning, a laboratory manual, Cold Spring Harbor Press, Cold Spring House, N.Y.

It is particularly preferred if the cytochrome P450 is a member of any one of the cytochrome P450 CYP1, CYP2, CYP3 or CYP4 families. It is still further preferred if the cytochrome P450 monooxygenase system is one which metabolises xenobiotics.

At least some members of the cytochrome P450 families CYP1, CYP2 and CYP3 are involved in the metabolism of xenobiotic compounds such as therapeutic drugs. Members of the cytochrome P450 CYP1 family are involved in the metabolism of, for example, caffeine, benzphetamine, phenacetin, theophylline, acetaminophen, antipyrine, 2-hydroxyestradiol, imipramine, tamoxifen and Zoxazolamine. Members of the cytochrome CYP2 family are involved in the metabolism of, for example testosterone, aflatoxin, benzphetamine, cyclophosphamide, hexobarbital, 6-aminochrysene, retinol, tolbutamide(methyl), phenytoin, S-warfarin, tienilic acid, diazepam, propanalol, amitryptyline, bufuralol, bupranolol, clozapine, codeine, debrisoquine, desipramine, dextromorphan, ethylmorphine, flecainide, haloperidol, lidocaine, nortryptilline, propanolol, sparteine, taxol, tetrahydrocannabinol, progesterone and mephenytoin.

Members of the cytochrome CYP3 family are involved in the metabolism of, for example, lovastatin, nifedipine, taxol, teniposide, testosterone, verapamil, vinblastine, vincristine, vindesine, benzphetamine, cortisol, cyclosporin A & G, diazepam, dihydroergotamine, estradiol, ethynylestradiol, imipramine and lidocaine.

More preferably the cytochrome P450 is any one of the P450s CYP3A4, CYP2D6, CYP2A6, CYP2E1, CYP2D9 and CYP2C9.

Conveniently, the cytochrome P450, apart from the adaptation to its N-terminus, consists essentially of the same polypeptide sequence as the native cytochrome P450. However, the term "cytochrome P450" specifically includes modifications to native cytochrome P450, for example, modifications which alter the length or other properties of any hydrophobic N-terminal portion which may be present in the native cytochrome P450 or modifications, such as single or multiple point mutations or deletions, which modify the substrate specificity of the cytochrome P450 compared to the native cytochrome P450.

By "cytochrome P450 reductase" we include any NADPH-cytochrome P450 oxidoreductase which is able to transfer electrons from NADPH to cytochrome P450. Mammalian cytochrome P450 reductase contains one each of FMN and FAD prosthetic groups. It is preferred if the cytochrome P450 reductase is derived from the same species as the cytochrome P450 expressed in the bacterial cell. It is particularly preferred if the cytochrome P450 reductase is a mammalian cytochrome P450 reductase; rat or human cytochrome P450 reductase are especially preferred. The human cytochrome P450 reductase cDNA is described in Smith et al (1994) *Proc. Natl. Acad. Sci. USA* 91, 8710-8714. The rat cytochrome P450 reductase cDNA is described in Porter et al (1990) *Biochemistry* 29, 9814-9818.

Cytochrome P450 reductase cDNAs and genes can readily be obtained using cloning methods well known in the art, some of which are described below.

Conveniently, apart from the adaptation to its N-terminus, the cytochrome P450 reductase consists essentially of the same polypeptide sequence of the native cytochrome P450 reductase. However, the term "cytochrome P450 reductase" specifically includes modifications to native cytochrome P450, for example single or multiple point mutations or deletions which modify the cofactor binding.

It is preferred that when the cytochrome P450 is a human cytochrome P450 the cytochrome P450 reductase is human cytochrome P450 reductase.

By "functional cytochrome P450 monooxygenase system" we mean that once the cytochrome P450 and cytochrome P450 reductase are expressed in the bacterial cell the cell, by virtue of the presence of said cytochrome P450 and said cytochrome P450 reductase, is able to convert a substrate for the cytochrome P450 monooxygenase system into a product provided that sufficient cofactors, such as NADPH and oxygen, are present.

By "functional coupling of said cytochrome P450 and said cytochrome P450 reductase within the cell" we mean that the cytochrome P450 and cytochrome P450 reductase are juxtaposed within the cell so that the cytochrome P450 reductase can provide electrons, whether directly or indirectly, to the cytochrome P450 during catalysis. The adaptation to the N-terminus of the cytochrome P450 or to the N-terminus of the cytochrome P450 reductase is merely one that allows functional expression and coupling of said cytochrome P450 and said cytochrome P450 reductase within the cell. The adaptation may be one which aids the juxtaposition of the cytochrome P450 and the cytochrome P450 reductase.

By "within the cell" we specifically include that the functional coupling may occur within or associated with any membrane or compartment of the cell including the periplasmic space or any membrane associated with the periplasm.

It is preferred if, the cytochrome P450 content of a culture of bacterial cells optimally expressing the cytochrome P450 is at least 100 nmol/l culture of whole cells, preferably at least 150 nmol/l culture of whole cells more preferably almost 250 nmol/l culture of whole cells, still more preferably about 500 nmol/l culture of whole cells and most preferably about 1000 nmol/l. Typically the cytochrome P450 content is around 200 nmol/l culture of whole cells.

Adaptions to each of the N-terminus of the cytochrome P450 and cytochrome P450 reductase which allow functional coupling of said cytochrome P450 and said cytochrome P450 reductase are discussed below.

Although not essential, it is preferred if the cytochrome P450 or cytochrome P450 reductase retains its own N-terminal sequence and that a further portion, such as a signal peptide as discussed below, is added to the N-terminus. of the cytochrome P450 or cytochrome P450 reductase or both.

Although it is envisaged that any aerobic or facultative anaerobic bacterial cell is suitable, it is preferred if the bacterial cell is Gram-negative and more preferred if the bacterial cell is a cell of a bacterium of the family Enterobacteriaceae, for example *Escherichia coli*. The Enterobacteria most closely related to *E. coli* are from the genus *Salmonella* and *Shigella* and less closely related are the genera *Enterobacter, Serratia, Proteus* and *Erwinia*. *E. coli* and *S. typhimurium* are the most preferred bacterial host cells for the present invention. Strains of *E. coli* K12 are most preferred because *E. coli* K12 is a standard laboratory strain which is non-pathogenic.

Although certain cytochrome P450 substrates are able to penetrate into the bacterial cell in order to be acted upon by the cytochrome P450 monooxygenase system it is preferred if the bacterial cell of the invention is one which has an increased permeability to a substrate or one which, when the bacterial cell is placed in an appropriate medium, becomes more permeable to the substrate. Additionally or alternatively it is preferred if the bacterial cell is one which has altered membrane properties, or a membrane whose properties can be altered, to facilitate the membrane penetration of the substrates. For example, a tolC mutant of *E. coli* has a more permeable membrane than a wild type *E. coli* (Chatterjee (1995) *Proc. Natl. Acad. Sci. USA* 92, 8950-8954) and the TA series of *S. typhimurium* strains have an increased permeability due to a deep rough mutation and have been frequently used for mutagenicity testing (see for example Simula et al (1993) *Carcinogenesis* 14, 1371-1376). *S. typhimurium* TA 97, 98, 100 and 102 as well as TA 1535 and TA 1538 have been used for mutagenicity testing in the pharmaceutical industry during drug safety evaluation. The present invention using these and other suitable bacterial strains are likely to improve these procedures, since they provide a humanized mutagenicity system and do not rely on rodent liver extracts (S9 fraction from rodent liver) as the metabolically activating system. The systems based on the present invention have also the advantage that the metabolically activating system and the target for mutagenicity, namely the DNA are within the same cell and are not physically separate entities as in the standard Ames test. This has the advantage that short lived metabolites are better detected and that the membrane barrier does not stop reactive metabolites to reach their DNA target. This, and other aspects of the invention, are discussed in further detail below.

It is also preferred if the cell is one which can be made more permeable by placing into the appropriate environment. Although there are many buffers systems which are suitable it is preferred if, following the expression phase, the bacterial cells, particularly *E. coli* cells, are resuspended in Tris-sucrose-EDTA, or TSE. TSE is 50 mM Tris. acetate (pH 7.6), 0.25 M sucrose, 0.25 mM EDTA. This may increase the permeability of the cells in several ways. Firstly, the cells are initially resuspended in double strength buffer, and then diluted rapidly with an equal volume of water. This has the effect of causing the release of periplasmic proteins, by rupturing the outer membrane momentarily. Secondly, EDTA is known to affect permeability directly, and can render cells more sensitive to certain hydrophobic agents. Thirdly, the Tris in the buffer can affect the structure of the lipopolysaccharide in the outer membrane, again altering permeability. Further details of ways to increase the permeability of the outer membrane of *E. coli* and *Salmonella typhimurium* is given in Nikaido & Vaara (1987) pp. 7-22 In: "*Escherichia coli* and *Salmonella typhimurium*. Cellular and Molecular Biology" Vol. 1. Ed. Neidhardt, F. C., Am. Soc. Microbiol., Washington D.C.

Advantageously, especially when the bacterial cells are used in a bioreactor, the cells are solvent-resistant. Solvent-resistant *E. coli* cells are known in the art for example from Ferrante et al (1995) *Proc. Natl. Acad. Sci. USA* 92, 7617-7621.

It is preferred if the cytochrome P450 reductase comprises an N-terminal portion which directs the cytochrome P450 reductase to a cellular compartment or membrane of the bacterial cell. It is particularly preferred if the said N-terminal portion directs the cytochrome P450 reductase to a membrane.

It is preferred if the cytochrome P450 and the cytochrome P450 reductase are associated with a membrane in the bacterial cell. It is particularly preferred if the cytochrome P450 and the cytochrome P450 reductase are associated with the bacterial inner membrane (particularly in the case of *E. coli* and *S. typhimurium*), with their active sites located in the cytoplasm.

In one preferred embodiment the N-terminal portion is one which is derived from or based on an N-terminal portion of a bacterial protein wherein said bacterial protein is one which is directed to the periplasmic space or one which is destined for secretion from the bacterial cell. For example, the *E. coli* proteins encoded by the ompA, pelB, malE or phoA genes are such bacterial proteins. It is desirable if the presence of the N-terminal portion aids the correct folding of the cytochrome P450 or cytochrome P450 reductase.

Bacterial leader sequences or signal peptides which direct bacterial proteins usually into the periplasm have been fused previously to the N-terminus of a few mammalian proteins with a view to exporting the resulting fusion proteins to the oxidising environment of the periplasm. Thus, such bacterial leader sequences or signal peptides have been used in the expression of mammalian secretory proteins such as immunoglobulins or fragments thereof. In contrast, mammalian xenobiotic-metabolising cytochrome P450s, when found in the endoplasmic reticulum in nature, are usually exposed to a reducing environment.

Thus, a particularly preferred embodiment is wherein the N-terminal portion comprises any one of the ompA, pelB, male or phoA signal peptides or leader sequences or a functionally equivalent variant thereof.

By "functionally equivalent variant thereof" we include any peptide sequence which, if present in place in the native said bacterial protein, would direct said protein to the same cellular location as the natural signal peptide.

It is preferred if the N-terminal portion of each of the cytochrome P450 and the cytochrome P450 reductase is a signal peptide or signal-peptide like N-terminal portion.

It is particularly preferred if the N-terminal portion is one which competes with the ompA leader for the general secretory pathway or competes with ompA for the signal recognition machinery, including the signal recognition particle and trigger factor.

The general secretory pathway and components thereof are described in Pugsley (1993) *Microbiol. Rev* 57, 50-108, incorporated herein by reference, and the signal recognition particle and trigger factor are described in Valent et al (1995) *EMBO J.* 14, 5494-5505, incorporated herein by reference. Competition assays between ompA signal peptide and a putative signal peptide can be carried out using methods known in the art using the teaching of Pugsley and Valent et al.

The pelB leader sequence consists of the amino acid sequence MKYLLPTAAAGLLLLAAQPAMA (SEQ ID No 1).

The ompA leader sequence consists of the amino acid sequence MKKTAIAIAVALAGFATVAQA (SEQ ID No 2).

Signal peptides have certain recognisable common features, which are detailed in von Heijne (1986) *Nucl Acids Res* 14, 4683-4690; Gierasch (1989) *Biochemistry* 28, 923-930; and the chapter by Oliver (1987) on Periplasm and Protein Secretion, pp. 56-69. Oliver (1987) In: "*Escherichia coli* and *Salmonella typhimurium* Cellular and Molecular Biology", Vol. 1, Ed. Neidhardt, F. C., Am. Soc. Microbiol, Washington D.C. Firstly, there is an N-terminal net positively charged region of variable length (n-region). This is followed by a hydrophobic core (h-region), of 10±3 amino acids, which is rich in Leu, Ala, Met, Val, Ile, Phe and Trp residues. Finally, there is the c-region of typically 5-7 amino-acids, which are generally slightly more polar than those in the h-region. The most important amino acids in this c-region are those at the −3 and −1 positions relative to the site of signal cleavage (the "−3, −1 rule")—there appear to be severe constraints on the possible amino-acids which can exist in these positions: only those with small side-chains are tolerated. Thus, only Ala, Gly, Leu, Ser, Thr and Val have been found at −3 (with Ala strongly preferred), and only Ala, Gly, Ser and Thr at −1 (with Ala again strongly preferred). Evidence suggests that β-turn formation in this signal processing region is important for signal cleavage to occur (see, for example, Barkocy-Gallagher et al (1994) *J Biol Chem* 269, 13609-13613, and Duffaud and Inouye (1988) *J Biol Chem* 263, 10224-10228.

It is preferred if signal peptide cleavage occurs. Thus, it is preferred if a suitable amino-acid sequence immediately downstream of the signal peptide, ie. in the protein to be expressed is included, since this still forms part of the "cleavage site". For example, a proline in position +1 inhibits signal removal (Barkocy-Gallagher et al (1992) *J. Biol. Chem.* 267, 1231-1238). Using ompA as an example, it may be that to ensure complete cleavage, if this is desirable, that the first few amino-acids of the mature ompA protein in the construct, immediately after the ompA leader, and immediately before the P450 or reductase sequence is included, Signal peptide cleavage is caused by a specific signal peptidase enzyme, for example signal peptidase I. In a preferred embodiment signal peptidase I is overproduced in the bacterial cell (for example, *E. coli*) to aid signal peptide cleavage if this is desirable (see van Dijl et al (1991) *Mol. Gen. Genet.* 227, 4048).

It is particularly preferred if the first two amino acids of the mature OmpA protein (ie. Ala Pro) are inserted immediately downstream of the ompA signal peptide and before the N-terminus of the P450.

Other preferred possibilities of increasing the probability of signal peptide cleavage is to introduce a short linker sequence between the signal peptide and the P450, or expression in different strains may lead to increased or reduced signal peptide cleavage compared with, for example, expression in DH5α.

Thus it will be seen that it is preferred if the N-terminal portion is a signal peptide which when present in its natural polypeptide has the function to mediate the membrane insertion and the export of the national polypeptide through the cytoplasmic membrane into the periplasmic space. Sequence of the leader sequence or signal peptide is usually up to 40 amino acid residues. It is envisaged that leaders can be modified without altering their functional properties.

In a further embodiment of the invention it is also preferred if the cytochrome P450 comprises an N-terminal portion which directs the cytochrome P450 to a cellular compartment or membrane of the bacterial cell. It is particularly preferred if the said N-terminal portion directs the cytochrome P450 to a membrane.

The preferred N-terminal portions in this embodiment are the same as the preferred N-terminal portions for the cytochrome P450 reductase. It is particularly preferred if the N-terminal portion of the cytochrome P450 comprises any one of the ompA, pelB, malE or phoA signal peptides or leader sequences, or a functionally equivalent variant thereof. The ompA signal peptide is particularly preferred.

In a further particularly preferred embodiment the N-terminal portion of the cytochrome P450 and the N-terminal portion of the cytochrome P450 reductase each direct the said cytochrome P450 or cytochrome P450 reductase to the same cellular compartment or membrane. This is particularly advantageous because it increases or improves the functional coupling of said cytochrome P450 and said cytochrome P450 reductase within the cell. It is particularly preferred if the cytochrome P450 and cytochrome P450 reductase are directed to the cytoplasmic side of the inner membranes where access is gained to the bacterial cytoplasmic NADPH pool.

In further preference the N-terminal portion of the cytochrome P450 is substantially the same as the N-terminal portion of the cytochrome P450 reductase.

In a further embodiment the cytochrome P450 comprises an N-terminal portion which is adapted to increase the translatability or correct folding of said cytochrome P450 in said bacterial cell.

Preferably, the cytochrome P450, compared to its native sequence, is modified at the N-terminus thereof.

By "translatability" we mean the efficiency with which a given RNA molecule can be translated into a polypeptide.

There are several features of the optimised CYP3A4 sequence which improve translatability.

These features include:

1. Second codon changed to suit *E. coli* preference (often GCT, encoding Ala). This is demonstrated by Looman et al (1987) *EMBO J* 6, 2489-2492.

2. Codons 4 and 5 made rich in A and T residues (where possible), to minimise the potential for mRNA secondary structure around the start codon. Minimisation of mRNA structure around the ribosome binding site and start codon can have large effects on the "translatability" (see, for example, Wang et al (1995) *Protein Expr Purif* 6, 284-290.

Concerning the use of leader sequences, the principal advantage is that by their nature, they are already "optimised" for bacterial expression, since they come from bacterial genes. This often includes the two features described above for example, both pelB and ompA leaders contain AAA (Lys) as the second codon, which was the best performing second codon in the paper of Looman et al in terms of "translatability". In addition, they often have reduced secondary structure around the ribosome binding site and start codon (see, for example, Movva et al (1980) *J Mol Biol* 143, 317-328 on ompA gene structure).

An additional advantage of using an N-terminal signal peptide fusion concerns the minimisation of any effect of rare codons in the P450 or reductase cDNA. For example, the AGA/AGG codon is the least used in *E. coli* (Chen and Inouye (1990) *Nucl Acids Res* 18, 1465-1473), and slows down translation as a result of the limiting availability of the corresponding charged tRNA molecule. However, the negative effect of such a rare codon reduces as its distance from the start codon increases (Chen & Inouye, supra). By adding an "optimised" bacterial leader sequence (typically 20-25 amino-acids in length) to the N-terminus of the P450 (or reductase), any rare codon close to the 5'-end of the P450 cDNA will be moved that much further away from the start codon, and therefore have much less effect.

Thus, it is preferred if "translatability" is improved by one or more of the following means:

1. Removal of rare codons (see Chen & Inouye, supra, such as AGG/AGA (Arg), CUA (Leu), AUA (Ile), CCC (Pro), and GGA/GGG (Gly) from the P450 or reductase cDNA, especially those less than 25-30 codons from the start codon.

2. As an alternative to, or in conjunction with, the above, introduction of genes encoding the rare tRNA synthases, for example, the dnaY gene for AGG/AGA.

3. Making other changes to the DNA sequence to reflect *E. coli* preferences, for example, the non-random utilisation of codon pairs (Gutman & Hatfield (1989) *Proc Natl Acad Sci USA* 86, 3699-3703).

4. Making changes to the promoter/ribosome binding site within the expression vector in order to minimise secondary structure potential and to optimise the distance between the ribosome binding site and the start codon (see Wang et al (1995), supra).

It is also preferred if the cytochrome P450 has its N-terminus modified according to U.S. Pat. No. 5,240,831 or, for example, by the general method of Gillam et al (1995) *Arch. Biochem. Biophys.* 317, 374-384, both of which are incorporated herein by reference.

The bacterial cell of the invention comprises a genetic construct capable of expressing a cytochrome P450 and a genetic construct capable of expressing a cytochrome P450 reductase.

Conveniently, the cell may contain one genetic construct capable of expressing both a cytochrome P450 and a cytochrome P450 reductase or the cytochrome P450 and the cytochrome P450 reductase may be expressed from separate genetic constructs.

The genetic construct may be DNA or RNA. DNA is preferred.

The genetic construct is typically an extrachromosomal genetic element such as a plasmid or bacteriophage genome but the term "genetic construct" specifically includes that the genetic construct may be part of the bacterial chromosome. For example, the genetic construct may be part of a bacteriophage which has lysogenised the bacterial chromosome.

The genetic construct comprises those genetic elements which are necessary for expression of the cytochrome P450 or cytochrome P450 reductase in the bacterial cell.

The elements required for transcription and translation in the bacterial cell include a promoter, a ribosome binding site, a coding region for the cytochrome P450 or cytochrome P450 reductase.

In terms of the promoter, it is believed that virtually any promoter functional in the selected bacterial cell may be employed. However, preferred promoters include the lac, lac UV5, tac, trc, $\lambda P_L$, T7, lpp, lpp-lac or T3 promoter. Of course, the $\lambda P_L$, T7 and T3 promoters are derived from bacteriophage and are known to be functional in bacteria such as *E. coli*.

The use of a regulatable promoter, such as the lac promoter, is preferred. It is preferred if a strong promoter, such as the T7 promoter, is not used.

One will often desire to incorporate an appropriate ribosome binding site for effecting bacterial expression into the eukaryotic cytochrome P450 domain comprising gene. Often, the ribosome binding site and promoter can be incorporated as a "cassette", defined as a contiguous, pre-fabricated DNA segment which incorporates the desired elements and has useful restriction enzyme recognition sites at its two termini, allowing it to be readily inserted at an appropriate point within the desired cytochrome P450 gene or cDNA or cytochrome P450 reductase by simple genetic manipulation.

Most conveniently, one may desire to simply employ a promoter and ribosome binding site from a homologous system, such as the lac promoter and its associated RBS. In general, however, it is proposed that one may employ any effective bacterial ribosome binding site, with those RBSs from *E. coli*, λ, T7 or T3 being preferred. Even more preferred ribosome binding sites are those from the T7 gene 10, or *E. coli* lac A, lac Z, trp A, trp B, trp C, trp D, trp E, trp L, trp R or trp S genes. A particularly preferred ribosome binding site and spacer region comprises the sequence 5'-AGGAGGT- CAT-3' (SEQ ID No 3), wherein the underlined portion comprises the ribosome binding site and the adjacent CAT sequence comprises the spacer region. (The spacer region is that sequence between the ribosome site and the ATG initiation codon.)

One will also typically desire to incorporate an appropriate bacterial transcription terminator, which functions to terminate the function of bacterial RNA polymerases, the enzymes responsible for transcribing DNA into RNA into a gene prepared in accordance with the invention. The requirements for a functional bacterial transcription terminator are rather simple, and are usually characterized by a run of T residues preceded by a GC rich dyad symmetrical region. The more preferred terminators are those from the TRP gene, the ribosomal terminators, rrnB, or terminator sequences from the T7 phage. In fact, the T7 terminator sequences contain RNase III cleavage sites with a stem-loop structure at the 3' ends of mRNAs which apparently slows down message degradation.

The genetic construct is capable of propagation in the bacterial cell and is stably transmitted to future generations.

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487-491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Suitably, the vectors include a prokaryotic replicon, such as the ColE1 ori, for propagation in a prokaryote. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

Transformation of appropriate cell hosts with a DNA construct of the present invention is accomplished by well known methods that typically depend on the type of vector used. With regard to transformation of bacterial host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y.

Electroporation is also useful for transforming cells and is well known in the art for transforming bacterial cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25 µFD.

Successfully transformed cells, ie cells that contain a DNA construct capable of expressing said cytochrome P450 or cytochrome P450 reductase, can be identified by well known techniques. For example, cells resulting from the introduction of an expression construct of the present invention can be grown to produce the cytochrome P450 or cytochrome P450 reductase. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

In a further preferred embodiment the bacterial cell further comprises a genetic construct capable of expressing a polypeptide cofactor which aids the correct folding of the cytochrome P450 or the cytochrome P450 reductase.

The presence of such a polypeptide cofactor is especially preferred when expressing the cytochrome P450 or the cytochrome P450 reductase from a strong promoter where, in the absence of the polypeptide cofactor, the cytochrome P450 or cytochrome P450 reductase may form non-functional inclusion bodies.

Preferably, the polypeptide cofactor is a molecular chaperone such as the Gro ELS complex, SecB, SecD, SecF, the DnaJ/DnaK/GrpE complex, peptidylprolyl-cis, trans isomerases, protein disulphide isomerase-like proteins encoded by the genes dsbA, dsbB, dsbC and dsbD, the periplasmic chaperone encoded by clpB or thioredoxin. The solubility of foreign proteins expressed in *E. coli* has been increased by the coproduction of bacterial thioredoxin (Yasukawa et al (1995) *J. Biol. Chem.* 270, 25328-25331; incorporated herein by reference).

It may also be useful to use the following systems or host or expression systems.

1. The use of protease-deficient strains of *E. coli* (for example, ompT⁻, lon⁻, degP⁻), which may reduce degradation of the expressed protein(s). A set of *E. coli* strains deficient in all known loci affecting proteolytic of secreted recombinant proteins is described in Meerman & Georgion (1994) *Biotechnology* 12, 1107-1110.

2. The expression of the P450 and/or reductase as a fusion protein with, for example, ubiquitin (Baker et al (1994) *J. Biol. Chem.* 269, 25381-25386), thioredoxin (eg pTrxFus vector from Invitrogen), glutathione S-transferase (eg pGEX vectors from Pharmacia) or protein A (eg pRIT2T vector from Pharmacia), any of which may enhance expression.

In a still further preferred embodiment the bacterial cell further comprises a genetic construct capable of expressing a polypeptide cofactor which aids transfer of electrons between the cytochrome P450 and the cytochrome P450 reductase. Preferably, the said cofactor is cytochrome $b_5$ or the FMN domain of a cytochrome P450 reductase.

Other cofactors which may aid the transfer of electrons include adrenodoxin/adrenodoxin reductase and NADH cytochrome $b_5$ reductase (in conjunction with cytochrome $b_5$). It is believed to be of particular benefit to use a cofactor which takes electrons from NADH, rather than NADPH in the present invention, or even to use both cofactors together, especially when dealing with whole cell metabolism ("bioreactors"). This is because the intracellular ratio of (NAD+NADH) to (NADP+NADPH) in *E. coli* is about 4:1. Therefore, there is a far greater potential for P450 reduction (and therefore enzyme activity) if the reducing equivalent is NADH rather than NADPH. In conjunction with this, the invention includes additions or modifications which may lead to an increase in the cytoplasmic pool of NADH and/or NADPH as a means of increasing enzyme activity in whole cells. This includes addition of precursors to the extracellular medium (those for which an uptake mechanism exists, such as nicotinamide), or inhibition of enzymes which destroy NADPH.

The FMN domain of cytochrome P450 reductase can be expressed as described in Smith et al (1994) *Proc. Natl. Acad. Sci. USA* 91, 8710-8714 and cytochrome $b_5$ can be expressed as described in Holmans et al (1994) *Arch. Biochem. Biophys.* 312, 554-565. It is preferred if a polypeptide cofactor which aids transfer of electrons is included when the cytochrome P450 is any one of CYP3A4, CYP3A5, CYP3A7, CYP2E1 and CYP1A1. It is particularly preferred if cytochrome $b_5$ is co-expressed with any one of CYP3A4, CYP3A5, CYP3A7 or CYP2E1.

It is also particularly preferred if the FMN domain is co-expressed with CYP1A1.

Although it is envisaged that in some instances the said cofactor may comprise an N-terminal portion which directs the cofactor to a cellular compartment or membrane of the bacterial cell, it is preferred if no such modifications are made to cytochrome $b_5$ or the FMN domain of cytochrome P450 reductase when they are expressed in the bacterial cell.

A further embodiment comprises a bacterial cell of the invention further comprising a genetic construct capable of expressing any one of an enzyme capable of metabolising the product of a reaction catalysed by the cytochrome P450 monooxygenase system.

In order to attempt to mimic to metabolism of a compound by a eukaryotic, especially mammalian, cell or an organ from an animal, especially a mammal, it is desirable to express in the bacterial cell of the invention one or more further polypeptides which, in the eukaryotic cell or in the animal may metabolise further the product of the cytochrome P450 monooxygenase system. This is particularly beneficial when the bacterial cell of the invention is used for mutagenicity testing or as a model for drug metabolism.

Conveniently, the enzyme is any of a glutathione S-transferase, an epoxide hydrolase or a UDP-glucuronosyl transferase. Other enzymes include sulfotransferase, N-acetyltransferase, alcohol dehydrogenase, γ-glutamyl transpeptidase, cysteine conjugate β-lyase, methyltransferase, thioltransferase, DT-diaphorase, quinone reductase or glyoxalase.

It will be appreciated that because several genetic constructs may be present in the same bacterial cell, for example constructs expressing cytochrome P450 and cytochrome P450 reductase and sometimes also cytochrome $b_5$ or an FMN domain of cytochrome P450 reductase or a further enzyme, it is convenient if bacterial strains are provided which have one or more of the genetic constructs integrated into their chromosome and that these strains can then be used as a "master" strain for the introduction of further genetic elements. For example, it is particularly preferred if the bacterial "master" strains comprise a cytochrome P450 reductase genetic construct integrated into the bacterial chromosome. It is also preferred if the bacterial "master" strains comprise a genetic construct or constructs which express both cytochrome P450 reductase and cytochrome $b_5$ from the bacterial chromosome. These "master" strains are then transformed with a genetic construct capable of expressing a cytochrome P450.

A further aspect of the invention provides a method of culturing a cell of the first aspect of the invention. Any suitable culture medium may be used. It is preferred if a nutrient-rich broth, such as Terrific broth, is used. It is also preferred if the culture medium contains a compound which aids haem synthesis; b-amino levulinic acid (ALA) is particularly preferred.

It will be appreciated that in all aspects of the invention where a bacterial cell contains two or more genetic constructs those genetic constructs are compatible with each other in the same bacterial cell. In general, genetic constructs which are integrated into the chromosome are compatible with one another and two genetic constructs are usually compatible with one another when one is integrated into the chromosome and the other is an autonomous replicon such as a plasmid. In general, when there are two or more different plasmids without the same cell which constitute the genetic constructs of the invention it is desirable if they are compatible plasmids, for example plasmids which have different origins of replication. It is also desirable if the different plasmids encode different antibiotic resistance genes so that all of the different plasmids can be selected when the bacterial cell is grown in culture.

A second aspect of the invention provides a method of converting a substrate for cytochrome P450 into a product, the method comprising admixing said substrate with a bacterial cell according to the first aspect of the invention wherein said cell contains a functional cytochrome P450 monooxygenase system which can convert said substrate.

A third aspect of the invention provides the use of a bacterial cell according to the first aspect of the invention for converting a substrate of a cytochrome P450 into a product.

The bacterial cells of the invention will find uses in many fields of technology, particularly those cells of the first aspect of the invention which express a functional cytochrome P450 monooxygenase system.

The following are some specific uses to which the bacterial cells of the invention can be put but it is envisaged that there are many other uses, for example whenever it is desirable to convert a cytochrome P450 substrate into a product.

a) Drug Development and Drug Testing

Bringing safe new drugs onto the market is expensive, complicated and protracted. Efficacy and safety of the market product, with respect to pharmacokinetic parameters, drug/drug interactions and toxicity, are critically dependent on the models employed for drug development. A major advance in drug development would result if the shortcomings of lead compounds could be predicted at the earliest stage of development.

There are serious problems in extrapolating pharmacotoxicological data from animal models to man. These are often due to pronounced species differences in the catalytic properties of drug metabolizing enzymes, which determine the pharmacological and the toxicological properties of most therapeutic drugs.

The bacterial cells, particularly E. coli and S. typhimurium cells, which form part of the present invention and which express functional P450 monooxygenase systems, are ideal models for mimicking human drug metabolism and are easier to handle than yeast and mammalian cell based models. These cells allow the high throughput screening of drugs with respect to optimized drug metabolism properties. This issue becomes particularly important with the advent of combinatorial chemical libraries which necessitate the evaluation of the drug metabolism properties of several hundred compounds within a short time.

In this embodiment it is useful if the bacterial cells also express other drug-metabolizing enzymes as described herein.

b) Bioreactors

The bacterial cells of the invention, because of the high substrate, regio and stereoselectivity of the oxidative reactions catalyzed by P450s are useful for the synthesis of fine or bulk chemicals and the synthesis of intermediates of chemical reactions.

In this embodiment it is clear that a bacterial cell of the invention is selected which expresses a cytochrome P450 with the appropriate substrate specificity. The substrate specificity of many cytochrome P450s is known in the art and so the appropriate cytochrome P450 can be readily selected. However, as more cytochrome P450 genes are found it will be possible to use those in the invention and, indeed, the bacterial cells of the invention, which express a new cytochrome P450 can be used to determine its substrate specificity.

It will be appreciated that because some cytochrome P450s are able to convert alkanes to alcohols or aromatic compounds to phenolic compounds the bacterial cells of the invention are useful in the bulk chemical industry where such alcohols and phenolic compounds are required. However, many of the reactions catalysed by cytochrome P450s make the cells of the invention useful in the fine chemical and pharmaceutical industries where selective oxidation (including hydroxylation) of complex structures is often required. It is believed that the cells of the invention are particularly suited to the synthesis of steroid hormones and analogues thereof.

c) Biocatalysis

The systems developed in the present invention will allow rapid functional testing of P450 variants generated by site directed mutagenesis. It will be therefore possible to generate within a short time novel P450s with improved catalytic properties.

d) Bio- and Chemo-Sensors

The bacterial cells of the invention are also useful as bio- or chemo-sensors. In particular membranes isolated from the cells are useful. Binding of substrates (which are the molecules to be sensed or detected) can cause a change of potential when the bacterial cell or the membranes isolated from the cell are present on an electrode surface thereby allowing detection of the substrate molecule. The use of immobilised cells for detection and analysis is described in Kambe & Nakanishi (1994) *Current Opinion in Biotechnology* 5, 54-59.

e) Bioremediation

The bacterial cells of the invention are also useful in bioremediation. For example, cytochrome P450 monooxygenase systems are able to detoxify harmful compounds. The appropriate bacterial cells expressing an appropriate cytochrome P450 which can oxidise the harmful compound is useful in rendering the said compound less harmless.

f) Carcinogenicity testing

As is described in more detail else where, the cells of the invention, particularly S. typhimurium cells, are useful in carcinogenicity testing.

Although it is envisaged that the cells of the invention are especially useful because they provide a functional cytochrome P450 monooxygenase system within an intact cell, it is also part of the invention that membranes are isolated from said cells and that said membranes are enriched in the cytochrome P450 monooxygenase system compared with whole cells. Membrane isolation from bacterial cells is well known in the art. Membrane isolation from cells of the invention is described in more detail in the Examples.

A fourth aspect of the invention provides a bacterial cell containing a cytochrome P450 said cell comprising a genetic construct capable of expressing, said cytochrome P450 wherein the cytochrome P450 comprises an N-terminal portion which directs the cytochrome P450 to a cellular compartment or membrane of the bacterial cell.

It is preferred if the N-terminal portion directs the cytochrome P450 to a membrane.

It is further preferred if the N-terminal portion comprises the ompA, pelB, malE or phoA signal peptide or a functionally equivalent variant thereof.

The preferred features of the N-terminal portion, particularly those of the signal peptides or leader sequences, are those preferred in the previous aspects of the invention.

It is still further preferred if the cytochrome P450 further comprises a peptide sequence which will aid purification of the cytochrome P450 from the bacterial cell; more preferably wherein said peptide sequence comprises a binding site for a compound.

It is particularly preferred if said peptide sequence is a -(His-)$_n$ where n≥4 and said compound is nickel.

It is contemplated that the fourth aspect of the invention is useful both for those cytochrome P450s which ordinarily couple with cytochrome P450 reductase and for other cytochrome P450s such as those which couple adrenodoxin/adrenodoxin reductase or equivalent electron transfer compounds. Thus, in a preferred embodiment of the fourth aspect of the invention, the cell further comprises a genetic construct capable of expressing each, or both, of adrenodoxin or adrenodoxin reductase of equivalent electron transfer components. By "equivalent electron transfer components" we include all other functionally-equivalent components which can transfer electrons from NADH to cytochrome P450, particularly those components whose natural function is to transfer electrons from NADH to particular cytochrome P450s.

A fifth aspect of the present invention provides a method of preparing is cytochrome P450, the method comprising the steps of (a) providing a sufficient quantity of cells according to the fourth aspect of the invention and (b) separating the cytochrome P450 from the other cellular compartments.

A further aspect of the invention provides a genetic construct capable of expressing a cytochrome P450 wherein the cytochrome P450 comprises an N-terminal portion which directs the cytochrome P450 to a cellular compartment or membrane of a bacterial cell. The preferred features of the N-terminal portion are those preferred in relation to the other aspects of the invention. It is particularly preferred if the N-terminal portion comprises the ompA, pelB, melE or phoA signal peptide or a functionally equivalent variant thereof. Other preferred features of the genetic construct are those preferred in the previous aspects of the invention. A still further aspect of the invention provides a plurality of bacterial cells of the first or fourth aspects of the invention, each cell containing a genetic construct capable of expressing a different cytochrome P450 or containing a genetic construct or constructs which encode different combinations of cytochrome P450 and cytochrome P450 reductase and, if appropriate, other polypeptides such as those which aid electron transfer or those which will further metabolise the product of the reaction of the cytochrome P450 monooxygenase system with a substrate.

Such a plurality (or library) of cells can conveniently be stored, for example in suitable conditions in a freezer and, for example, in a microtitre plate, each well containing a different bacterial cell. The plurality of cells may be useful for drug-testing or carcinogenicity testing and for other purposes such as those described above.

The invention is described in more detail below with reference to the following Examples and Figures.

FIG. 1: Construction of pB216

Plasmid NF14 was modified by replacement of an existing transcription terminator by an annealed oligonucleotide pair consisting of a trpA terminator with SalI and BglII ends. This modification removed a second BglII site, allowing subsequent cloning at the remaining BglII site, and creating the plasmid pB215. A BclI-BglII fragment containing pelB-reductase with a $P_{tac}P_{tac}$ promoter was subcloned from pB207 into the BglII site of pB215, to make the co-expression plasmid pB216. The orientation of the pelB-reductase insert was found to be as shown.

Figure 2:
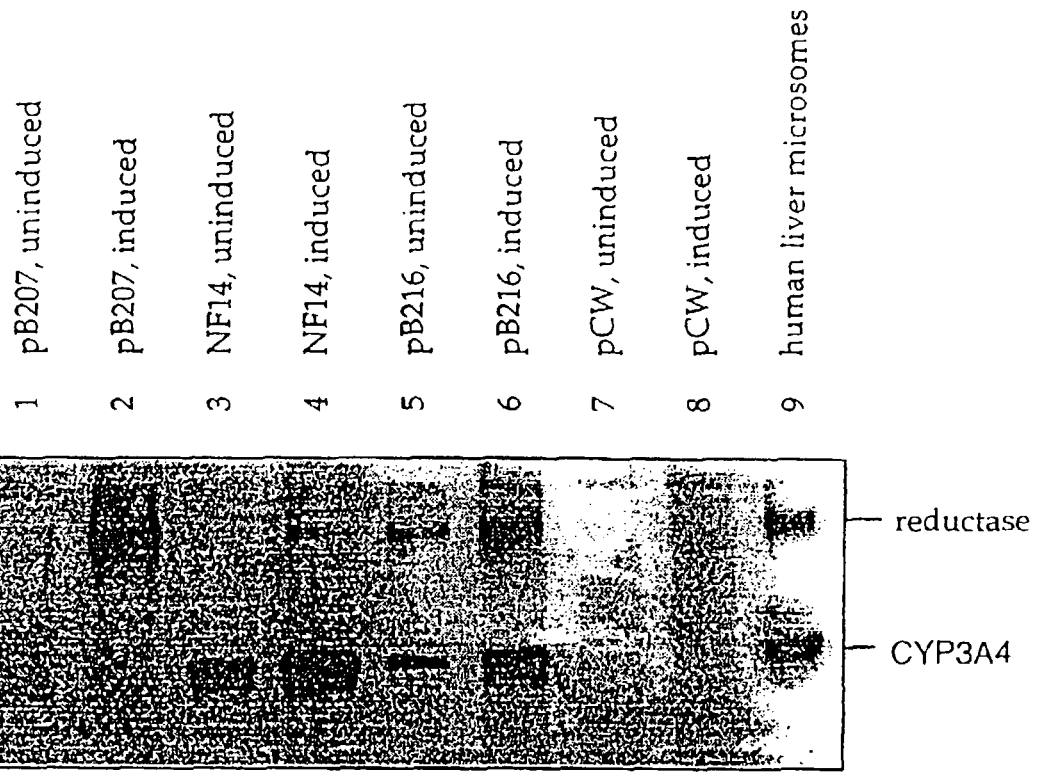

FIG. 2: Western blot of membrane fractions containing reductase and CYP3A4 expressed in *E. coli*

10 µg of each membrane fraction was loaded onto each track. The order of loading is shown along the top of the blot. Each expression sample is shown alongside its uninduced counterpart. The immunodetection was carried out using antibodies against reductase and CYP3A. A human liver microsome track (10 µg microsomal protein) was included as a reference track.

Figure 3:
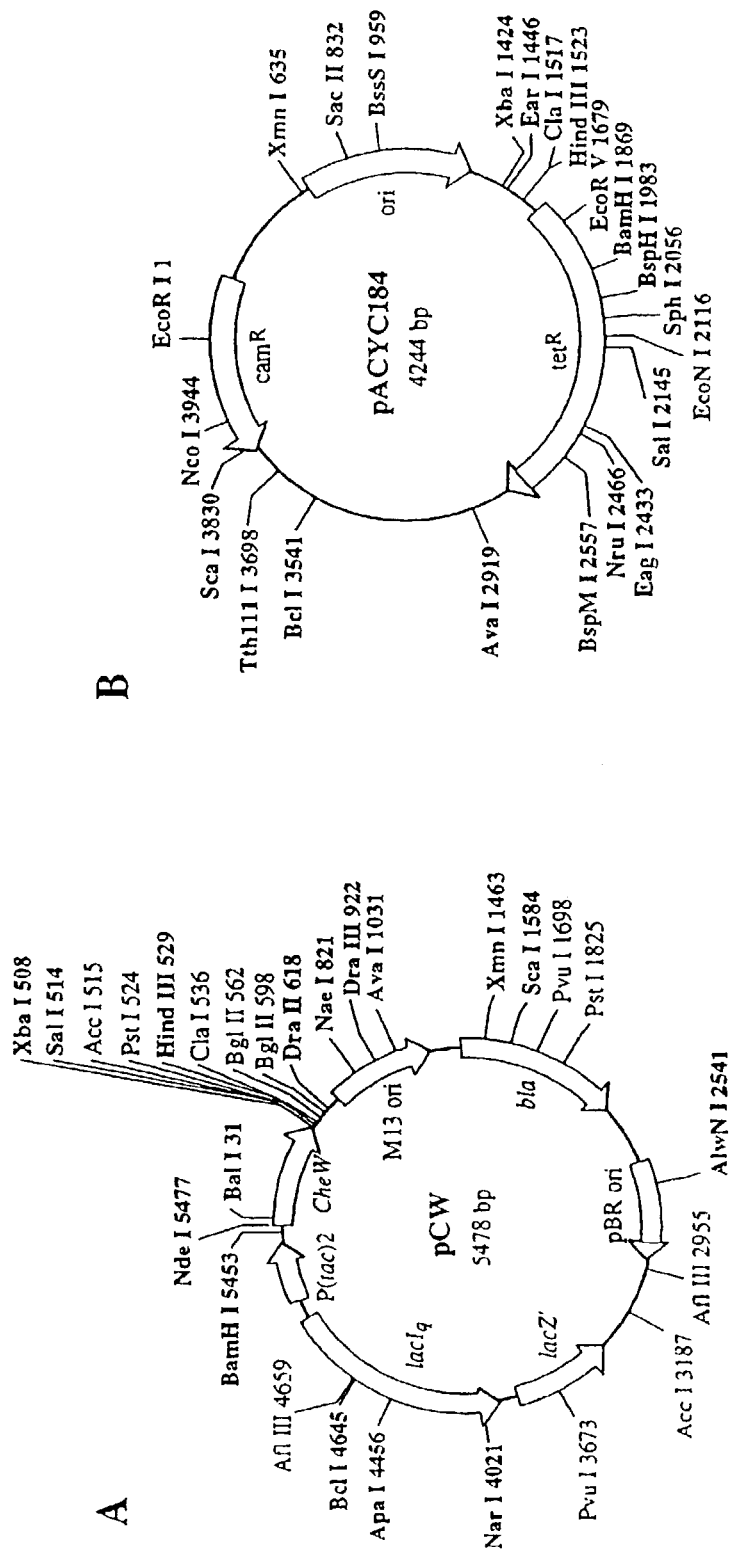

FIG. 3: A representation of the two expression vectors used in this study.

Plasmid pCW (FIG. 3A) contains a colE1 origin of replication and the beta-lactamase gene, giving resistance to antibiotics such as ampicillin and carbenicillin. It was used for the expression of the P450 cDNAs. Plasmid pACYC184 (FIG. 3B) contains a p15A origin of replication, and was used for expression of the P450 reductase cDNA, when a P450 cDNA was being concomitantly expressed from pCW. The antibiotic used for selection of pACYC184 was chloramphenicol. Unique restriction sites are shown in bold.

Figure 4:
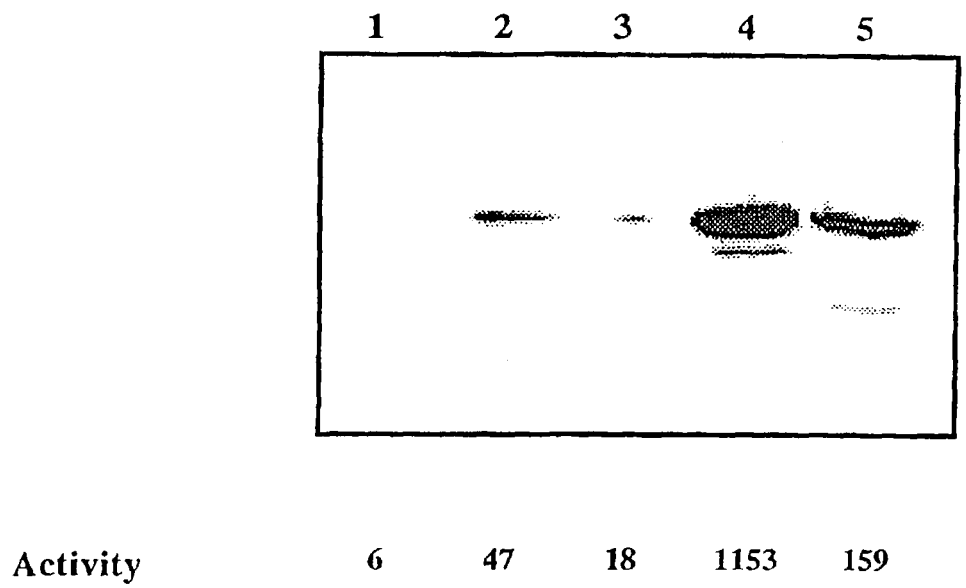

FIG. 4: Western blot showing expression of P450 reductase in bacterial membranes.

Proteins were separated by SDS-PAGE, transferred onto nitrocellulose membrane, and then probed with rabbit anti-reductase primary antibody and horseradish peroxidase-linked anti-rabbit IgG secondary antibody. Detection was by chemiluminescence. Protein loading was 10 µg per track. Expression of the wild-type P450 reductase cDNA under non-inducing and inducing conditions is shown in tracks 1 and 2, respectively. Corresponding expression of a bacterial pelB leader-P450 reductase N-terminal fusion protein is shown in tracks 3 and 4. A sample of human liver microsomes is shown in track 5 for comparison. Reductase activities (in nmol cytochrome c reduced per min per mg protein) are given below the figure.

Figure 5:
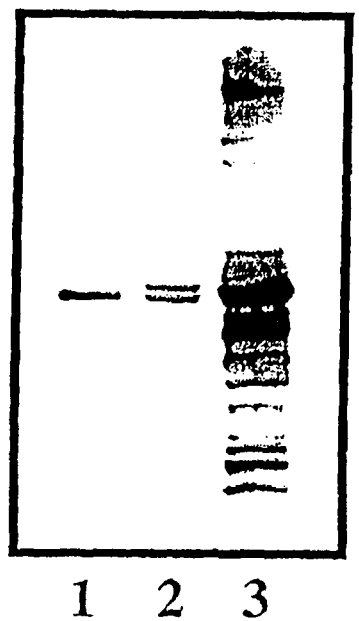

FIG. 5: Western blot showing the expression of pelB- and ompA-CY3A4 in bacterial membranes.

Proteins were separated by SDS-PAGE on a 9% acrylamide gel, transferred onto nitrocellulose, and probed with rabbit anti-CYP3A primary antibody and horseradish peroxidase-linked anti-rabbit IgG secondary antibody. Detection was by chemiluminescence. Lanes 2 and 3 contain membranes isolated from bacteria expressing either pelB-CYP3A4 or ompA-CYP3A4, respectively (24 µg protein per track). Lane 1 contains a sample of human liver microsomes for comparison (8 µg protein).

Figure 6:
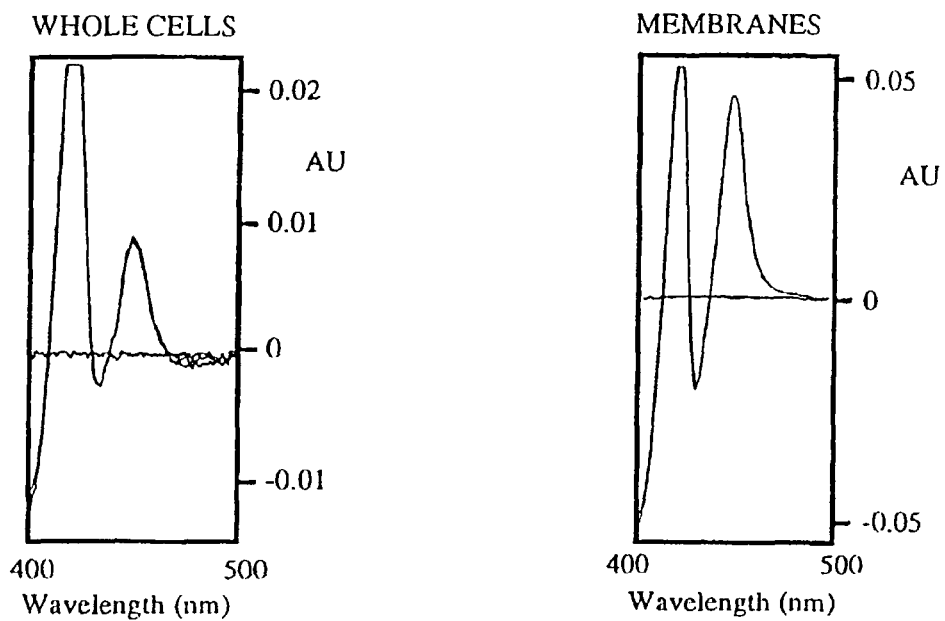
Figure 6:
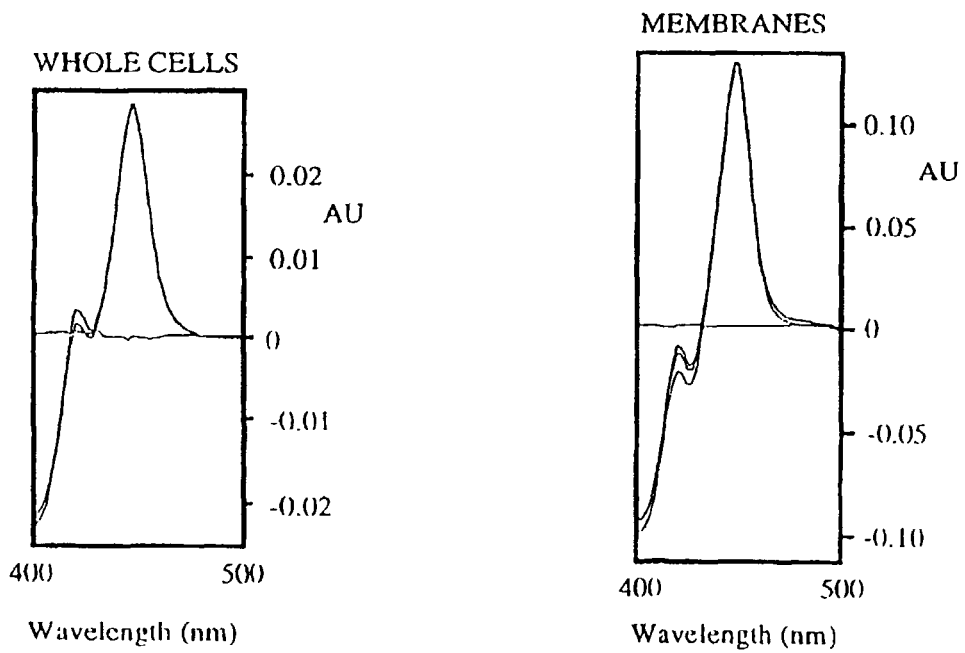

FIG. 6: Reduced Fe—CO spectra obtained from whole bacteria expressing pelB-CYP3A4 (FIG. 6A) ompA-CYP3A4 (FIG. 6B), or membranes derived from these cells.

Aliquots of cells or membranes were diluted 1:20 into 100 mM Tris-HCl, pH 7.4, containing 20% glycerol, 10 mM CHAPS and 1 mM EDTA, reduced by the addition of a few crystals of sodium dithionite, and then divided equally between a pair of matched glass cuvettes. Following determination of a baseline spectrum over the range 500 to 400 nM, the sample cuvette was bubbled gently with CO for about 1 minute. The scan was then repeated, and P450 content estimated using an extinction coefficient of 91 $mM^{-1} cm^{-1}$.

FIG. 7: Summary of the expression levels of CYP3A4 from different constructs in *E. coli*, as estimated from the reduced Fe—CO difference spectra (see above).

Results are expressed as mean±SD, with the number of determinations in parentheses. Cells were grown under standardised conditions (Terrific Broth, 30° C., 24 h induction) ±0.5 mM δ-ALA.

Figure 8:
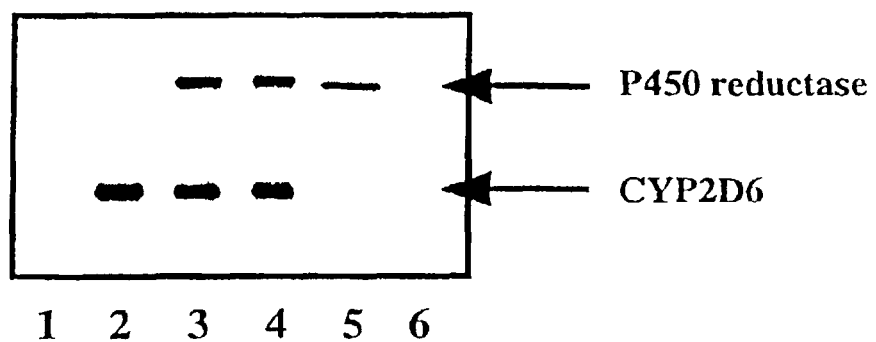

FIG. 8: Western blot showing the expression of ompA-CYP2D6 in bacterial membranes.

Proteins were separated by SDS-PAGE on a 9% acrylamide gel, transferred onto nitrocellulose, and then probed with a mixture of rabbit anti-CYP2D6 and anti-reductase primary antibodies, followed by horseradish peroxidase-linked anti-rabbit IgG secondary antibodies. Detection was by chemiluminescence. Tracks 1 to 4 each contain 2.5 µg bacterial membrane protein. Track 5 contains 10 µg human liver microsomes, and track 6 protein standards. Membranes were isolated from cells carrying the empty expression vector, pCW (lane 1), ompA-2D6 alone (lane 2), or ompA-2D6 plus P450 reductase, cultured either in the absence (lane 3) or presence (lane 4) of the haem precursor delta-aminolevulinic acid.

Figure 9:
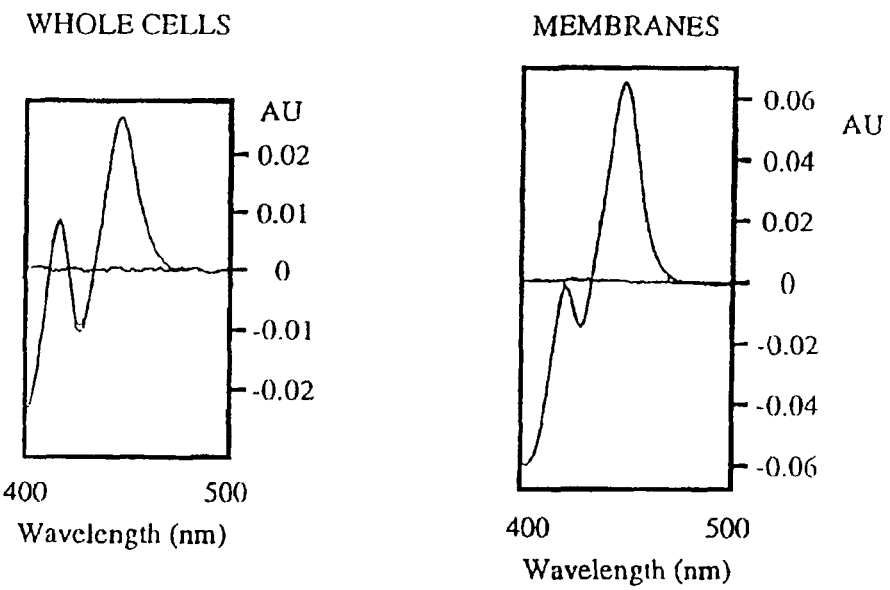
Figure 9:
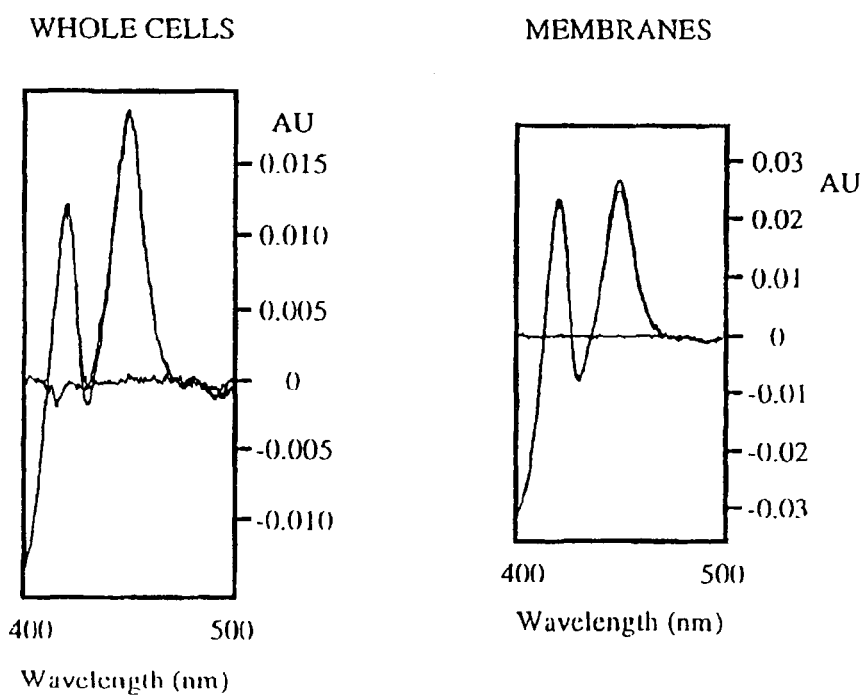

FIG. 9: Reduced Fe—CO spectra obtained from whole bacteria expressing ompA-CYP2D6 alone (FIG. 4A), ompA-CYP2D6 co-expressed with P450 reductase (FIG. 4B), or membranes derived from these cells.

Aliquots of cells or membranes were diluted 1:20 into 100 mM Tris-HCl, pH 7.4, containing 20% glycerol, 10 mM CHAPS and 1 mM EDTA, reduced by the addition of a few crystals of sodium dithionite, and then divided equally between a pair of matched glass cuvettes. Following determination of a baseline spectrum between 500 and 400 nm, the sample cuvette was bubbled gently with CO for about 1 min. The scan was then repeated, and P450 content estimated using an extinction coefficient of 91 mM$^{-1}$ cm$^{-1}$.

FIG. 10: Summary of the observed levels of ompA-CYP2D6 when expressed alone or co-expressed with P450 reductase in *E. coli*, as estimated from the reduced Fe—CO spectra (see above).

Results are expressed as mean±SD, with the number of determinations in parentheses. Cells were grown under standardised conditions (Terrific Broth, 30° C., 24 h induction) ±0.5 mM δ-ALA.

Figure 11:
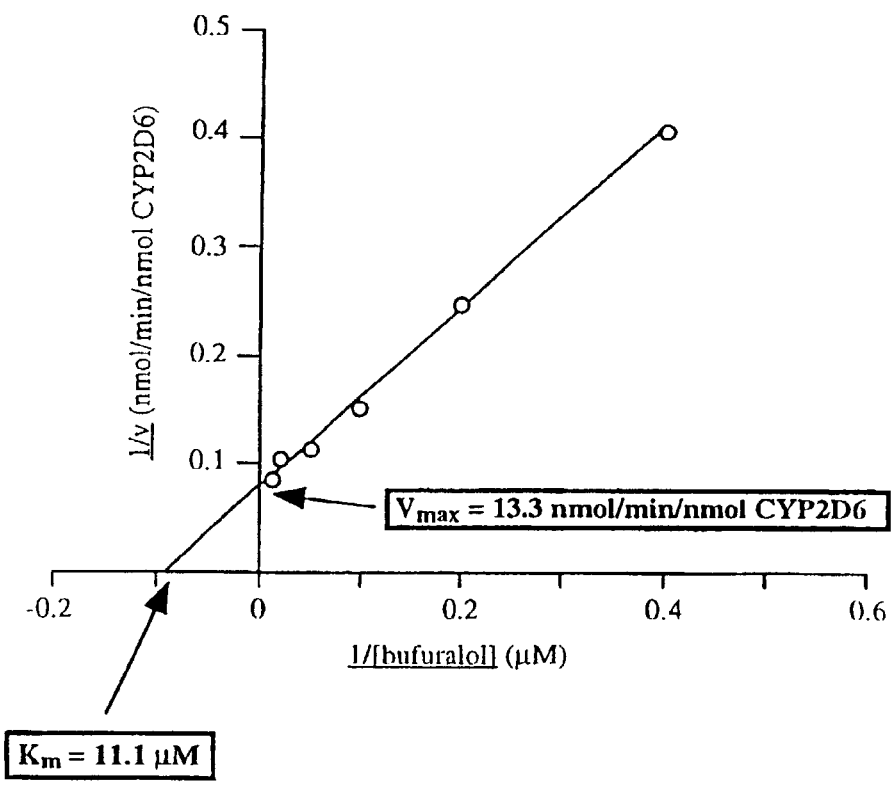

FIG. 11: Kinetic parameters determined for the 1'-hydroxylation of bufuralol in bacterial membranes co-expressing ompA-CYP2D6 and P450 reductase.

Membranes were incubated at 37° C. with varying concentrations of substrate (0-100 µM) in the presence of a NADPH generating system, under conditions which gave linear product formation with respect to protein and time (not shown). The extent of product formation was assessed by reversed-phase HPLC, with reference to authentic standard. Kinetic parameters were estimated from a double-reciprocal plot of initial velocity against substrate concentration.

FIG. 12: P450 yield achieved in *E. coli* using the gene fusion strategy in comparison to the yield obtained by others after modifying the P450 N-terminus by deletions and mutations.

Figure 13:
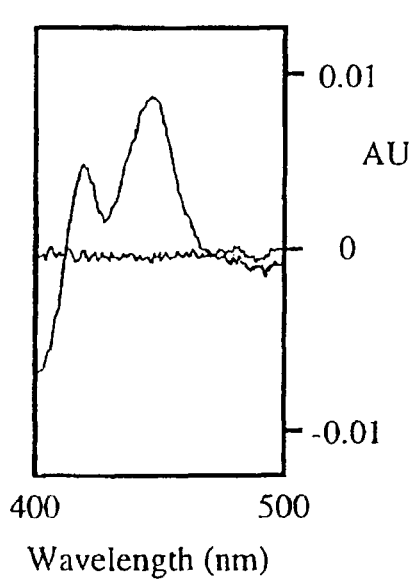
Figure 13:
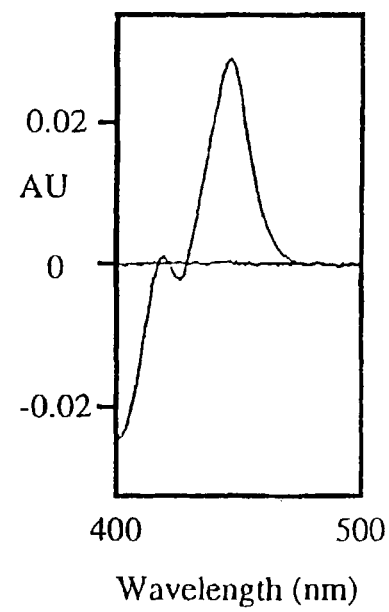

FIG. 13: Reduced Fe—CO spectra obtained from whole bacterial expressing ompA-CYP2A6, or from membranes derived from these cells.

Aliquots of cells or membranes were diluted 1:20 into 100 mM Tris-HCl, pH 7.4, containing 20% glycerol, 10 mM CHAPS and 1 mM EDTA, reduced by the addition of a few crystals of sodium dithionite, and then divided equally between a pair of matched glass cuvettes. Following determination of a baseline spectrum between 500 and 400 nm, the sample cuvette was bubbled gently with CO for 1 min. The scan was repeated, and P450 content estimated using an extinction coefficient of 91 mM$^{-1}$ cm$^{-1}$.

FIG. 14: Summary of the observed levels of ompA-CYP2A6 when expressed in *E. coli*, as estimated from the reduced Fe—CO spectra (see above).

Results are expressed as mean±SD, n=3. Cells were grown under standardised conditions (Terrific Broth, 30° C., 24 h induction) in the presence of δ-aminolevulinic acid (0.5 mM).

Figure 15:
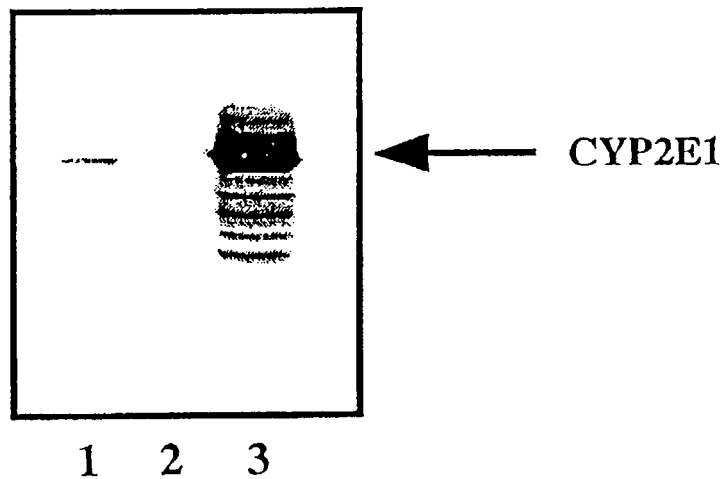

FIG. 15: Western blot showing the expression of ompA-CYP2E1 in bacterial membranes.

Proteins were separated by SDS-PAGE on a 9% acrylamide gel, transferred onto nitrocellulose, and probed with sheep anti-CYP2E1 primary antibody and horseradish peroxidase-linked anti-sheep IgG secondary antibody. Detection was by chemiluminescence. Lane 2 contains membranes isolated from control bacteria harbouring the empty expression plasmid, pCW, and lane 3 membranes isolated from bacteria expressing ompA-CYP2E1 (24 µg protein per track in each case). Lane 1 contains a sample of human liver microsomes for comparison (8 µg protein).

Figure 16:
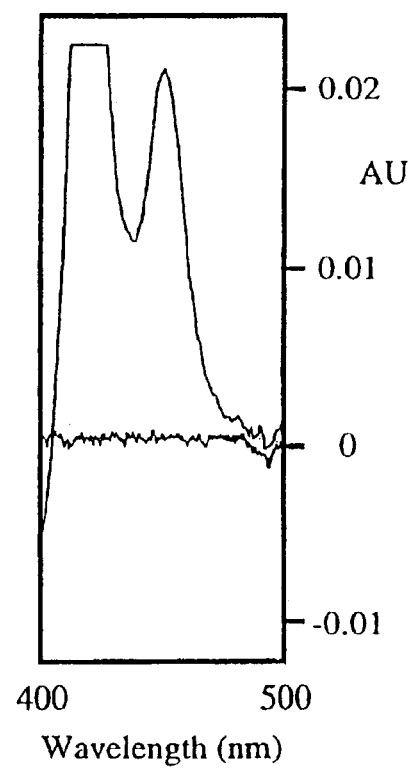

FIG. 16: Reduced Fe—CO spectra obtained from whole bacteria expressing ompA-CYP2E1.

Aliquots of cells were diluted 1:20 into 100 mM Tris-HCl, pH 7.4, containing 20% glycerol, 10 mM CHAPS and 1 mM EDTA, reduced by the addition of a few crystals of sodium dithionite, and then divided equally between a pair of matched glass cuvettes. Following determination of a baseline scan from 500 to 400 nm, the sample was bubbled gently with CO for 1 min. The scan was repeated, and P450 content estimated using an extinction coefficient of 91 mM$^{-1}$ cm$^{-1}$.

Expression level: 451 nmol/l culture in whole cells.

Figure 17:
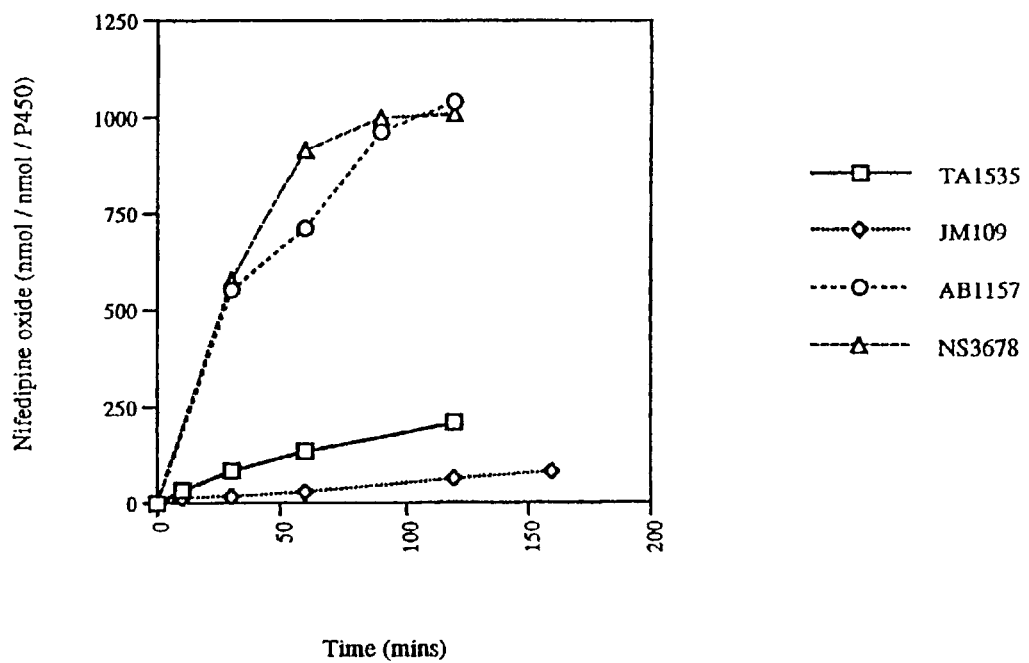

FIG. 17: Metabolism of nifedipine by CYP3A4 in intact JM109, AB1157, NS3678 and TA1535 [pB216] cells Incubations were carried out in M9 salts supplemented with glucose (10 mM) at 37° C. with shaking (200 rpm). 0.5 ml of 10× concentrated cells was added to 4.5 ml of buffer and pre-equilibrated at 37° C. for 5-10 min before addition of nifedipine to a final concentration of 200 µM. At intervals 200 µl aliquots were removed and processed for HPLC analysis as described in Materials and Methods, in Example 4.

Figure 18:
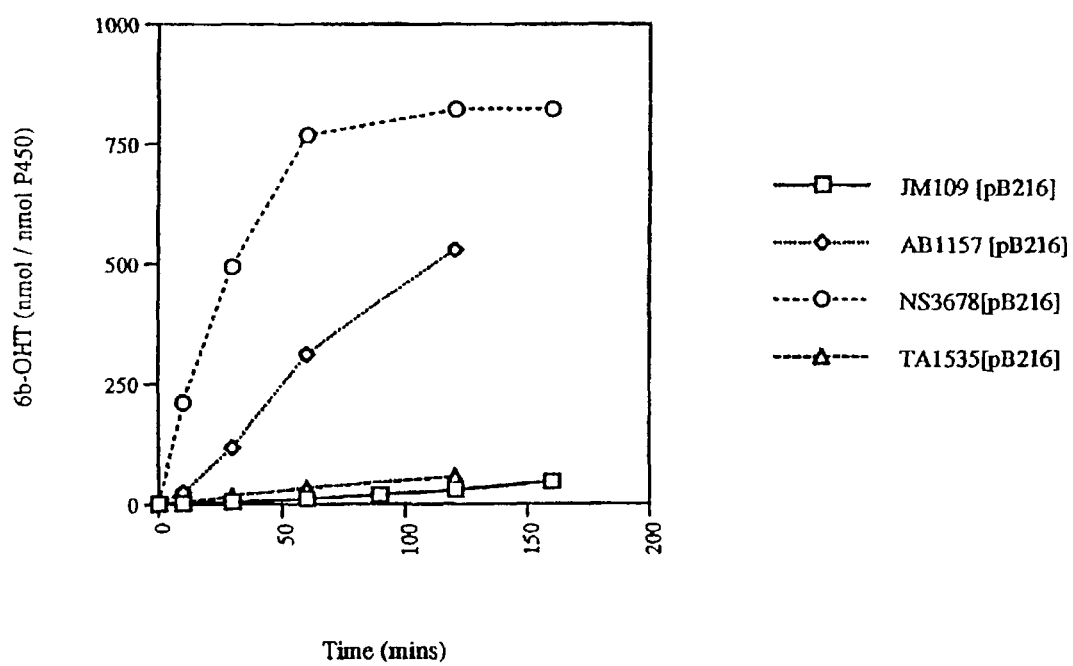

FIG. 18: Metabolism of testosterone by CYP3A4 in intact JM109, AB1157, NS3678 and TA1535 [pB216] cells Incubations were carried out in M9 salts supplemented with glucose (10 mM) at 37° C. with shaking (200 rpm). 0.5 ml of 10× concentrated cells was added to 4.5 ml of buffer and pre-equilibrated at 37° C. for 5-10 min before addition of testosterone to a final concentration of 200 µM. At intervals 200 µl aliquots were removed and processed for HPLC analysis as described in Materials and Methods, in Example 4.

EXAMPLE 1

Materials and Methods

Bacterial Strains and Plasmids

Co-expression was compared in the *E. coli* K12 strains JM109 (Yanisch et al (1985) *Gene* 33, 103-19) and DH5α (Woodcock et al (1989) *Nucleic Acids Res* 17, 3469-78), and the strain selected and used throughout was JM109. The vector pCW was used for the expression of reductase, as this has previously been used successfully for expression of several mammalian P450 cDNAs, including CYP3A4 (Gillam et al (1993) *Arch. Biochem. Biophys.* 305, 123-131). The plasmid pB207 comprises the pCW vector containing the human reductase cDNA translationally fused to the bacterial pelB signal sequence. The sequence of the 5' end of the cDNA is: [ATGAAATACCTGCTGCCGACCGCTGCT-GCTGGTCTGCTGCTCC TCGCTGCCCAGCCGGC-GATGGCCATGGATATCGGATCCGAATT CCGCAA-CATG-human reductase cDNA (~2 kb)] (SEQ ID No 4), where the pelB leader sequence is shown underlined and the native reductase ATG is shown in bold. NF14 (pCW containing an optimised CYP3A4 sequence) was constructed in such a way as to be identical to that of Gillam et al (Gillam et al (1993) *Arch. Biochem. Biophys.* 305, 123-131). Plasmid pB215 was constructed by replacing the SalI-BglII fragment of NF14 that contains a transcription terminator with a SalI-BglII double-stranded oligonucleotide containing a trpA transcription terminator of the following sequence (top strand only shown): TCGACAGCCCGCCTAAT-GAGCGGGCTTTTTTTA (SEQ ID No 5). A BclI-BglII fragment from pB207 containing the pelB-reductase cDNA with its expression signal was subcloned into pB215 at the unique BglII site to create pB216.

Co-Expression of CYP3A4 and Reductase in *E. coli*

Expression conditions were a modification of those described previously (Gillam et al (1993) *Arch. Biochem. Biophys.* 305, 123-131). JM109 cells were transformed with pB216 as described (Inoue et al (1990) *Gene* 96, 23-8) and transformants isolated on LB agar plates containing 50 µg/ml ampicillin. Single colonies were prepared, and were used to inoculate 5 ml starter cultures in LB broth containing ampicillin, which were grown with shaking at 37° C. overnight. Expression cultures were generally 100 ml cultures (in 1 l flasks) containing Terrific Broth modified and supplemented as described (Gillam et al (1993) Arch. Biochem. Biophys. 305, 123-131). Expression cultures were inoculated with 1 ml overnight culture and grown shaking at 200 rpm, 30° C. for 4-5 h prior to induction with 1 mM IPTG and addition of 0.5 mM δ-aminolevulinic acid. Growth and expression of heterologous proteins was then continued for 20-24 h at 30° C. with 200 rpm shaking.

Harvesting Cultures and Determination of Expression Levels

Cells were harvested and resuspended in 5 ml 100 mM Tris. acetate (pH 7.6), 0.5 M sucrose, 0.5 mM EDTA (2×TSE) as described (Gillam et al (1993) Arch. Biochem. Biophys. 305, 123-131). An equal volume of ice-cold distilled water was then added. The CYP3A4 content was determined using $Fe^2$—CO vs $Fe^{2+}$ difference spectra by adding 50 μl whole cell suspension in 1×TSE to 950 μl 100 mM Tris. Cl (pH 7.4), 10 mM CHAPS, 20% v/v glycerol, 1 mM EDTA and reducing by adding a few grains of sodium dithionite. A baseline of zero absorbance was recorded between 500 and 400 nm, then the sample cuvette was bubbled under a steady stream of CO for about 1 minute. A spectrum was then recorded and the yield of spectrally active CYP3A4/1 culture determined. At this stage, an aliquot of whole cells was withdrawn for metabolism studies. Membrane fractions were isolated from the remaining cells as described (Gillam et al (1993) Arch. Biochem. Biophys. 305, 123-131). The CYP3A4 and reductase content of the membranes was determined. The yield of active reductase was evaluated by a spectrophotometric assay, as follows. To 990 μl 50 μM cytochrome c in 0.3 M potassium phosphate buffer (pH 7.7), 1-10 μg membrane protein was added, and a baseline recorded. 50 μM NADPH was added and $\Delta A_{550\ nm}$ was recorded over time. To determine the P450 contents of membranes, spectra were obtained as for whole cells.

Immunodetection of Heterologously Expressed CYP3A4 and Reductase

10 μg membrane protein was loaded per track onto a SDS-9% polyacrylamide gel, and the proteins separated by electrophoresis. Proteins were then transferred to an ECL-nitrocellulose membrane (Amersham), blocked with 10% milk powder in TBS-T [50 mM Tris. Cl (pH 7.9), 150 mM NaCl, 0.05% Tween-20] for 20 minutes, then incubated with diluted primary antibodies for up to 1 h (a mixture of rabbit anti-CYP3A and anti-reductase immunoglobulins were used). The membrane was then washed in TBS-T, and incubated in diluted HRP-linked donkey anti-rabbit antisera for about 45 minutes. After washing, reductase and CYP3A4 were detected using ECL reagents (Amersham). Anti-reductase and anti-CYP3A4 antisera were provided by the ICRF Clare Hall facility, whereas HRP-linked donkey anti-rabbit antibodies were obtained from the Scottish Antibody Production Unit.

Testosterone 6β-hydroxylase Assays

Assays were carried out with cells and membrane fractions. In both cases, approximately 100 pmol P450 was incubated with shaking in TSE containing 30 mM $MgCl_2$. The final testosterone concentration was 0.2 mM. Where membranes were used, an NADPH generating system was is added (final concentration 1 mM NADP, 5 mM glucose-6-phosphate, 1 unit glucose-6-phosphate dehydrogenase). Reactions were carried out at 37° C. for 5 minutes, then stopped by addition of 1 ml ice-cold methanol and placed on ice for 10 minutes. Following centrifugation, supernatants were diluted with an equal volume of ice-cold water, and the testosterone metabolites extracted using Isolute C18 columns (IST Ltd), and eluted in 1 ml methanol. The methanol was evaporated in a SpeedVac, and the metabolites then resuspended in 200 μl 35% v/v methanol, and transferred to HPLC vials. Metabolites were separated by HPLC on a Spherisorb ODS-2 (5 μm) 250×4.6 mm column using a gradient based on water, methanol and acetonitrile, at a flow rate of 1 ml/min, and detected at 240 nm. The yield of the 6β-hydroxytestosterone was calculated by reference to a standard of known concentration, and this allowed determination of the specific activity of the recombinant CYP3A4 towards testosterone. The HPLC method was supplied by Glaxo-Wellcome, and testosterone metabolites by Steraloids Inc. (a gift from Sterling Winthrop).

Erythromycin N-demethylase Assays

Bacterial membrane fractions were incubated with 0.5 mM erythromycin in 50 mM HEPES buffer (pH 7.5) containing 150 mM KCl and 10 mM $MgCl_2$ in the presence of NADPH generating system (as above), for 20 minutes at 37° C. The reaction was then stopped by the addition of 7.5% w/v trichloroacetic acid, and the protein precipitate collected by centrifugation. The erythromycin N-demethylase activity was then determined by a spectrophotometric assay performed using Nash reagent [6M ammonium acetate, 60 mM acetyl acetone, 150 mM acetic acid; (Nash (1953) Biochem. J 55, 416-421], measuring $A_{412\ nm}$.

Nifedipine Oxidase Assays

Cells or membrane fractions were incubated with 0.2 mM nifedipine in TSE containing 30 mM $MgCl_2$ at 37° C. for 10 minutes with shaking. Where membrane fractions were used, NADPH generating system was included (as above). The reactions were stopped by adding ice-cold methanol (30% v/v final concentration) and perchloric acid (1.5 v/v final concentration) and the precipitated protein collected by centrifugation. The supernatants were transferred to HPLC vials and nifedipine and its oxidised metabolite were separated isocratically on a Spherisorb ODS-2 (5 μm) 250×4.6 mm column using a mobile phase of methanol, acetonitrile and water (25:30:45 by volume), and detected at 254 nm by HPLC. The amount of product formed was calculated by reference to a standard containing a known concentration of oxidised nifedipine.

Results

Construction of a Plasmid for Co-expression of CYP3A4 and Reductase

Preliminary experiments to optimise expression of reductase in E. coli indicated that high levels of controllable expression were achieved when the human reductase cDNA was translationally fused at its N-terminal to the bacterial pelB leader sequence and expressed from the $P_{tac}P_{tac}$ promoter of pCW, in the plasmid designated pB207; these expression levels were substantially higher than those obtained from the comparable construct lacking the pelB leader (data not shown). These results are consistent with the previous expression of rat reductase fused to another bacterial signal sequence, ompA (Shen et al (1989) *J. Biol. Chem.* 264, 7584-7589). A co-expression plasmid was constructed by subcloning the pelB-reductase cDNA into the optimised CYP3A4 expression plasmid NF14 (Gillam et al (1993) *Arch. Biochem. Biophys.* 305, 123-131) (reconstructed for the present work) as follows. NF14 was modified by removing one of the BglII restriction sites within the vector, thereby allowing the downstream BglII site to be used for the subsequent cloning of reductase while retaining the terminator of CYP3A4 expression (see Methods and Materials and FIG. 1 for details; pB215). A BclI-BglII fragment from pB207 containing the pelB-reductase cDNA and its $P_{tac}P_{tac}$ promoter was then subcloned into pB215 at the BglII site, creating a plasmid, pB216, in which the two cDNAs, each bearing the $P_{tac}P_{tac}$ promoter, were arranged head-to-tail (see FIG. 1).

Optimisation of Co-expression of Reductase and CYP3A4 from pB216

The ideal culture conditions were found to be similar to those established to be optimal for expression of CYP3A4 from NF14 (Gillam et al (1993) *Arch. Biochem. Biophys.* 305, 123-131), except that supplementation of cultures with δ-aminolevulinic acid was found to substantially increase expression of CYP3A4 (unpublished data), and is therefore now routinely used. Expression levels in the *E. coli* strains JM109 and DH5α were compared, and it was found that while the level of expression of reductase was slightly higher in DH5α than in JM109, this was at the expense of the CYP3A4 level (data not shown). JM109 was consequently selected as the expression strain, as it was decided that the level of CYP3A4 expression should be considered the priority.

Previous reports of expression of reductase in *E. coli* indicated that the growth medium was supplemented with riboflavin (Shen et al (1989) *J. Biol. Chem.* 264, 7584-7589). We found that the addition of riboflavin made negligible difference to the level of expression of active reductase, so riboflavin was therefore not included in the expression cultures.

Determination of Expression Levels

CYP3A4 content can be determined in whole bacterial cells using $Fe^{2+}$—CO vs $Fe^{2+}$ difference spectra, but for the assessment of reductase expression levels, bacterial membrane fractions were prepared as described (Gillam et al (1993) *Arch. Biochem. Biophys.* 305, 123-131). This was necessary because the reductase assay measures the rate of reduction of cytochrome c, and the background activity measured in JM109 cells is prohibitively high to allow direct determination from cells or spheroplasts. For expression of reductase from pB216, the specific activity of reductase obtained was in the range of 400 pmol reductase/mg membrane protein, as calculated by rates of reduction of cytochrome c by membrane preparations. The CYP3A4 content measured in membranes was typically around 200 pmol/mg membrane protein. Thus after co-expression of CYP3A4 and reductase from pB216, the bacterial membranes contain approximately a 2:1 ratio of P450 reductase to P450.

Immunodetection of Heterologously Expressed CYP3A4 and Reductase

A typical western blot showing heterologously expressed reductase and CYP3A4 is shown in FIG. 2. Bands corresponding to reductase and CYP3A4 can be detected in the membrane fractions derived from pB216 (tracks 5 and 6), while reductase alone and CYP3A4 alone can be detected in those samples derived from pB207 (tracks 1 and 2) and NF14 (tracks 3 and 4) respectively. Expression was not entirely repressed under non-inducing conditions, as observed from the appearance of reductase and CYP3A4 bands in tracks derived from bacterial cultures in which their expression had not been induced by the addition of IPTG (tracks 4 and 6). However, the amounts of active reductase and spectrally active CYP3A4 derived from these fractions was found to be much lower than those derived from the induced cultures (data not shown), and this might therefore indicate that the detection of the bands is not a linear response to the content of CYP3A4 and reductase in the samples. The amounts of heterologously expressed CYP3A4 and reductase in the JM109 pB216 membrane fractions appeared similar to those detected in a sample of human liver microsomes (tracks 6 and 9).

Assays of CYP3A4 Activity in Whole Cells

Whole JM109 pB216 cells were found to metabolise testosterone. No 6β-hydroxytestosterone was detected after incubation of testosterone with the negative control strains JM109 pCW (vector only) or JM109 pB207 (reductase expression only). This shows that *E. coli* is unable to catalyse 6β-hydroxylation of testosterone in the absence of CYP3A4. Cells expressing CYP3A4 alone (JM109 NF14) also did not produce detectable levels of metabolite, indicating that there is no endogenous protein in JM109 that can supply electrons to CYP3A4 thereby allowing catalytic function. When 100 μM cumene hydroperoxide was added to a reaction containing JM109 NF14 cells, however, 6β-hydroxytestosterone was formed. This infers that the CYP3A4 in JM109 NF14 cells is functional, but that there is no available intracellular supply of electrons. The low activity achieved may reflect an inaccessibility of the P450 to cumene hydroperoxide within whole cells. On co-expression of CYP3A4 with reductase, a relatively high rate of testosterone metabolism occurs (JM109 pB216 sample). This indicates that co-expressed reductase and CYP3A4 couple in whole cells to produce a functional monooxygenase system.

In this experiment, the 6β-hydroxylase activity was calculated to be ~17.3 nmol 6β-hydroxytestosterone produced/minute/nmol P450. Previous results with a reconstituted system containing bacterially-expressed CYP3A4 have obtained turnover rates of up to 10 nmol 6β-hydroxytestosterone/minute/nmol P450 (Gillam et al (1993) *Arch. Biochem. Biophys.* 305, 123-131).

Metabolism of Testosterone, Erythromycin and Nifedipine by JM109 pB216 Membranes Membrane fractions derived from pB216 were found to mediate metabolism of the CYP3A4 substrates testosterone, nifedipine and erythromycin without supplementation by phospholipids, detergent, glutathione or cytochrome $b_5$. In these assays, membrane fractions containing 100 pmol CYP3A4 were simply incubated with substrate in the presence of NADPH generating system. Typical activities are shown in Table 2. The results indicate that JM109 pB216 membrane fractions are proficient for metabolism of three CYP3A4 substrates. The erythromycin N-demethylase activity was ~2.5-fold less than previously observed in reconstituted systems containing bacterially-expressed CYP3A4 (Gillam et al (1995) *Arch. Biochem. Biophys.* 317, 374-384). In contrast, however, the nifedipine oxidase activity was similar to that previously observed for a reconstituted system (Gillam et al (1993) *Arch. Biochem. Biophys.* 305, 123-131).

TABLE 1

Cytochrome P450 content and cytochrome c reductase activities of JM109 NF14 and JM109 pBZ16 cells and/or membranes

|  | P450 Content | | Reductase activity |
| --- | --- | --- | --- |
|  | nmol/l culture* | pmol/mg† | nmol cyt c reduced/ min/mg |
| pCW | n.d. | n.d. | 38 ± 16 |
| NF14 | 222 ± 35 | 350 ± 50 | 30 ± 3 |
| pJR4 | n.d. | n.d | 1355 ± 380 |
| pB216 | 200 ± 45 | 215 ± 35 | 1315 ± 321 |

P450 contents were measured by $Fe^{2+}$-CO vs $Fe^{2+}$ difference spectra. Contents are expressed as means of 4 experiments ± SD.
*Content was measured in 50 µl cells in 1 × TSE (~0.5 ml culture).
†Content was assessed per mg protein in membrane fractions derived from recombinant bacteria.
Reductase activities were calculated by measuring the rate of reduction of cytochrome c per mg protein in membrane fractions, and values are given as means of four experiments ± SD.
n.d. = no detectable activity.

TABLE 2

CYP3A4-dependent metabolism of testosterone, nifedipine and erythromycin by JM109 pB216 cells and membranes

|  | Turnover $(min^{-1})$ | | | | |
| --- | --- | --- | --- | --- | --- |
|  | Testosterone | | Nifedipine | | Erythro- |
|  | cells | membranes | cells | membranes | mycin* |
| pCW | <0.5 | <0.5 | <2 | <2 | <0.3 |
| NF14 | <0.5 | <0.5 | <2 | <2 | <0.3 |
| pJR4 | <0.5 | <0.5 | <2 | <2 | <0.3 |
| pB-216 | 17.3 ± 3.3 | 25.5 ± 4.3 | 15.2 ± 1.3 | 12.7 ± 0.9 | 2.3± 0.7 |

* For erythromycin metabolism, activities could only be recorded with membranes, as the background level of formaldehyde formation by whole cells was very high.

Metabolism of three known CYP3A4 substrates by cells or membranes containing recombinant CYP3A4 and P450 reductase was assessed. Turnover numbers are recorded as nmol product formed/min/nmol P450, and are shown ±SD. The products which were detected were 6β hydroxytestosterone, oxidised nifedipine and formaldehyde. Where no activities were detected, detection levels are shown. For testosterone metabolism, no 6β hydroxytestosterone was formed even after 60 minutes incubation with cells or membranes lacking either CYP3A4 or P450 reductase (data not shown).

Discussion

In this Example we describe the generation of a functional P450 monooxygenase system in *E. coli*, by co-expression of the cDNAs encoding human CYP3A4 and P450 reductase. To our knowledge, this is the first instance in which a mammalian xenobiotic-metabolising P450 has been shown to be catalytically active in intact *E. coli* cells. While the steroidogenic P450 17α-hydroxylase/17-, 20-lyase (P450c17) is functional in *E. coli*, by virtue of its ability to accept electrons from the bacterial flavodoxin/NADPH-flavodoxin reductase system (Jenkins et al (1994) *J. Biol. Chem.* 269, 27401-27408), *E. coli* cells expressing CYP3A4 alone (JM109 NF14 cells) did not metabolise the CYP3A4 substrate testosterone in the absence of an exogenous supply of electrons (in this case from cumene hydroperoxide). We therefore conclude that CYP3A4 cannot couple with this or another bacterial reductase.

We developed a system for co-expression of CYP3A4 and human P450 reductase in *E. coli*, in order that these cells might be of use as biocatalysts for production of valuable P450 metabolites. Both cDNAs were expressed under separate $P_{tac}P_{tac}$ promoters in a single plasmid, pB216, so that coordinate expression of the CYP3A4 and reductase could be induced by IPTG. To achieve optimal levels of expression, both cDNAs were modified from their original form. The 5' end of the CYP3A4 cDNA was modified as previously described (Gillam et al (1993) *Arch. Biochem. Biophys.* 305, 123-131). For efficient expression of P450 reductase, we found that it was necessary to extend the 5' end of the cDNA by fusion with the sequence encoding the bacterial pelB signal peptide. Yields of CYP3A4 of 200 pmol/mg membrane protein, and reductase yields 400 pmol/mg membrane protein were obtained.

We believe that the co-expressed CYP3A4 and pelB-reductase may be localised on the same face of the bacterial cytoplasmic membrane, as JM109 pB216 cells and membranes isolated from them are active towards CYP3A4 substrates, indicating that the proteins must be able to couple efficiently. Activities measured towards the substrates were found to be higher than previous results obtained with purified bacterially-expressed CYP3A4 in a reconstituted system (Gillam et al (1993) *Arch. Biochem. Biophys.* 305, 123-131; Gillam et al (1995) *Arch. Biochem. Biophys.* 317, 374-384). Such reconstituted systems contain purified CYP3A4, reductase, cytochrome $b_5$, glutathione, detergent and an optimised phospholipid composition. Cytochrome $b_5$ has been shown to be important in obtaining maximal CYP3A4 activities against particular substrates for a CYP3A4-reductase fusion protein (Shet et al (1993) *Proc. Natl. Acad. Sci. USA* 90, 11748-11752), while the phospholipid composition and glutathione concentration was also shown to be critical in a reconstituted system containing CYP3A4 (Gillam et al (1993) *Arch. Biochem. Biophys.* 305, 123-131). In the absence of these ancillary factors, CYP3A4 activity towards testosterone was rather unexpected in whole cells and in membranes within the simple buffer system used here. It was therefore extremely interesting that, in our studies, high levels of CYP3A4 activity towards these substrates was observed in the absence of exogenously added cytochrome $b_5$.

In summary, we have successfully achieved high level co-expression of CYP3A4 and human P450 reductase in *E. coli*. The resulting strain is proficient for whole cell metabolism of testosterone and nifedipine even in the absence of exogenously applied NADPH, suggesting that (at least) the reductase active site is cytoplasmically orientated. Membranes derived from the bacteria metabolise testosterone, nifedipine and erythromycin in a simple buffer supplemented only with NADPH. The specific activities achieved from our co-expression strain are higher than previously obtained with reconstituted systems. We hope to investigate the possible reasons for this discrepancy to improve the turnover rates. The strain described in the present Example will be of use as a biotechnological tool for production of CYP3A4 metabolites, and will be used as a model system for future co-expression of alternative P450 isoforms with P450 reductase in *E. coli*.

EXAMPLE 2

Materials and Methods

Bacterial Strains and Plasmids

The *E. coli* K-12 strain JM109 (Yanisch et al (1985) *Gene* 33, 103-19) was used throughout. Cytochrome P450 cDNAs were expressed from the plasmid pCW. This plasmid includes a β-lactamase gene, and can therefore be stably maintained in bacterial cells grown in the presence of an agent such as ampicillin or carbenicillin. The human P450 reductase cDNA was expressed from the plasmid pACYC184, which can be stably maintained in bacterial cells in the presence of chloramphenicol.

Isolation of Bacterial Signal Peptide Coding Sequences and Generation of Expression Constructs The source of the coding sequence for the bacterial pelB signal peptide was the commercial vector pET-20b (Novagen). Chromosomal DNA was extracted from *E. coli* strain JM109 and used as the template for the isolation of the ompA leader sequence by PCR, using specific oligonucleotide primers. This PCR product was sub-cloned and subjected to dideoxy sequencing, and was found to be identical to an ompA leader sequence already registered in the Gen-EMBL database (accession number:v00307), namely: 5'ATGAAAAAGACAGCTATCGCOATTG-CAGTGGCACTGGCTGG TTTCGCTACCGTAGCGCAG-GCC-3' (SEQ ID No 6)

A PCR fusion technique (Yon et al (1989) *Nucleic Acids Res.* 17, 4895) was used to fuse the coding sequence for the bacterial pelB or ompA signal peptide in frame to the 5'-end of the full length P450 cDNA. Using this method, we made pelB-CYP3A4, ompA-CYP3A4, ompA-CYP2D6, ompA-CYP2A6, and ompA-CYP2E1 fusions, engineering in each case a NdeI restriction site at the 5' end of the construct to facilitate sub-cloning into pCW. All PCR-derived fragments were verified by dideoxy sequencing.

The pelB-human reductase construct described previously was sub-cloned, together with an upstream (tac)$_2$ promoter cassette, as a BclI-BglII fragment into the unique BamHI site of the plasmid pACYC184, to produce plasmid pJR7.

Expression in *E. coli* of Human P450s Fused to Bacterial Leader Sequences

JM109 cells were transformed with pCW/pelB-CYP3A4, pCW/ompA-CYP3A4, pCW/ompA-CYP2D6, pCW/ompA-CYP2A6, or pCW/ompA-CYP2E1 (Inoue et al (1990) *Gene* 96, 23-28). Transformed cells were selected with ampicillin and amplified for further study. For co-expression, JM109 cells were co-transformed with the plasmids pCW/ompA-CYP2D6 and pJR7, and selected on both ampicillin and chloramphenicol.

A standard protocol was used for all expression and co-expression experiments. Transformants were streaked from a frozen glycerol stock onto LB agar plates containing either ampicillin alone (for P450 expression) or ampicillin plus chloramphenicol (for co-expression of P450 and reductase), and incubated at 37° C. for 12-14 h. Single isolated colonies were then inoculated into a few ml of LB broth (containing the appropriate antibiotic(s)) and shaken overnight at 37° C. This starter culture was diluted 1:100 into 100 ml Terrific Broth modified and supplemented as described (Gillam et al (1993) *Arch. Biochem. Biophys.* 305, 123-131), but with chloramphenicol (25 µg/ml) added when reductase was being co-expressed, in a 1 l conical flask. These cultures were incubated at 30° C. for 4-5 h with shaking. The haem precursor δ-aminolevulinic acid was then added to a final concentration of 0.5 mM, and the inducing agent IPTG to 1 mM. Expression of heterologous proteins was then allowed to proceed for 22-23 h at 30° C.

Harvesting Cultures and Determination of Expression Levels—As Described Previously

Immunodetection of Heterologously Expressed P450 and Reductase

Proteins were separated on SDS-9% acrylamide gels and then transferred onto Hybond-ECL membrane (Amersham, UK). The membrane was blocked with 5% milk powder in TBS-X [50 mM Tris. Cl (pH 7.9), 150 mM NaCl, 0.10% Triton X-100] for 1 h, then incubated with diluted primary antibodies for 45-60 min. The primary antibodies used were rabbit anti-CYP3A, rabbit anti-CYP2D6, rabbit anti-reductase, or sheep anti-CYP2E1 immunoglobulins. The membrane was washed in four changes of TBS-X, and then incubated with the secondary antibody (HRP-linked donkey, anti-rabbit or anti-sheep IgG, as appropriate) for 25-35 min. After four washes with TBS-X, the recombinant proteins were detected by chemiluminescence using ECL (Amersham, UK). Secondary antibodies were obtained from the Scottish Antibody Production Unit.

Bufuralol 1'-hydroxylase Assays

Assays on bacterial membrane fractions were carried out at 37° C. in 50 mM potassium phosphate buffer, pH 7.4, containing 20 or 50 pmol CYP2D6, 50 µM (±)-bufuralol, and a NADPH regenerating system (see Example 1) in a total volume of 300 µl. For membranes isolated from cells carrying pCW/ompA-CYP2D6 only (ie. no reductase co-expressed), the NADPH regenerating system was replaced by 100 µM cumene hydroperoxide. Reactions were stopped by the addition of 15 µl of 60% perchloric acid and placed on ice for 5-10 min. Precipitated proteins were removed by centrifugation, and then the supernatants were analysed for 1'-hydroxybufuralol by reversed-phase HPLC, with reference to authentic standard. Separation was achieved using a Spherisorb 5 µm ODS-2 column 25 cm×4.6 mm, and a mobile phase of 0.1 M ammonium acetate (pH 5.0) with a linear gradient of acetonitrile (27 to 51% in 12 min). Detection was by fluorescence using excitation and emission wavelengths of 252 and 302 nm, respectively.

Assays on whole cells were carried out at 37° C. in 50 ml conical flasks, and contained 50 pmol CYP2D6, 50 µM (±)-bufuralol and 1×TSE buffer in a total volume of 5 ml. Samples (300 µl) were withdrawn at 0, 2, 5 and 10 min into tubes containing 15 µl of 60% perchloric acid on ice. Analysis then proceeded in an identical manner to the membrane assays (see above).

For the determination of Michaelis-Menten kinetic parameters, incubations were carried out for 5 min with 20 pmol CYP2D6 and varying concentrations of substrate (0 to 100 µM). $K_m$ and $v_{max}$ were estimated from double-reciprocal plots of initial reaction velocity versus substrate concentration.

Results

Isolation of P450 and P450-reductase cDNAs

The cDNAs for CYP3A4, CYP2D6, CYP2A6 and CYP2E1 and P450-reductase were isolated by RT-PCR using amplimers which were synthesized based on the published sequence information. The cDNAs were verified by DNA-sequencing and found to encode proteins with primary structures identical to those published for CYP3A4, CYP2D6, CYP2A6 and CYP2E1 and the human P450-reductase.

Construction and expression of human P450 reductase fused to the pelB leader sequence P450 reductase is required for the catalytic activity of human P450s and is absent in *E. coli*. We tried to express the native P450 reductase or the P450 reductase fused at its N-terminus to the pelB leader sequence (MKYLLPTAAAGLLL-LAAQPAMA-) (SEQ ID No 1) in *E. coli*. Initially we tried to express both proteins under the control of the IPTG (isopropylthiogalactoside) inducible $(tac)_2$ promoter in the plasmid pCW (FIG. 3). Membranes were isolated from *E. coli* harbouring the native P450-reductase and the pelB-reductase and were analysed by immunoblotting (FIG. 4). In the absence of IPTG, negligible amounts of P450 reductase were detected, and a clear induction of the recombinant protein was observed upon addition of IPTG. Expression of the native P450 reductase from the plasmid pJR1 was low, whereas high levels of pelB-P450 reductase were achieved from the plasmid pJR2. These differences were also reflected in the P450-reductase activity towards cytochrome c detected in membranes containing these two recombinant proteins. In these preparations the pelB-reductase displayed an almost ten fold higher reductase activity as compared to the native P450 reductase (FIG. 4). These results clearly demonstrate that optimal expression of functional P450 reductase in *E. coli* is only possible after fusion of this protein to a bacterial leader sequence.

Construction and Expression of CYP3A4 Fused to Bacterial Leader Sequences

CYP3A4 is the major human liepatic P450 (Shimada et al (1994) *J. Pharmacol. Exp. Ther.* 270, 414-423) and is involved in the metabolism of a wide variety of therapeutic drugs as well as chemical carcinogens. In order to achieve efficient expression of this important P450, we constructed a series of modified CYP3A4 cDNAs which encode the CYP3A4 fused at its N-terminus to either the bacterial pelB or the bacterial ompA leader sequence (MKKTAIAIAVALAG-FATVAQA) (SEQ ID No 2) using a PCR based strategy which has been shown to allow the fusion of any two sequences at any site (Yon et al (1989) *Nucleic Acids. Res.* 17, 4895). The resulting cDNA constructs were sequenced, cloned into the vector pCW and were transformed into the *E. coli* strain JM109 for expression.

Colonies which grew in the presence of ampicillin were selected for further DNA and protein analysis. *E. coli* harbouring the expression constructs were grown in terrific broth and P450 expression was induced by IPTG as described in Materials and Methods. CYP3A4 expression was detected by immunoblot analysis of bacterial membranes (FIG. 5) and by spectral analysis of whole cells or membranes (FIG. 6). As can be seen from FIG. 5, the level of immunoreactive pelB-CYP3A4 was similar to the CYP3A4 level found in human liver microsomes, whereas the level of immunoreactive ompA-CYP3A4 was at least an order of magnitude higher. Interestingly, pelB-CYP3A4 yielded two closely migrating immunoreactive proteins. A similar result was also obtained after purification of a His-tagged pelB-3A4 by nickel-agarose affinity chromatography, whereas ompA-3A4 which had been purified similarly yielded a homogeneous protein. pelB-CYP3A4 and ompA-3A4 displayed a $Fe^{2+}$ vs. $Fe^{2+}$—CO spectrum typical for P450 haemoproteins (FIG. 6). The yield of spectrally active pelB-CYP3A4 but not of ompA-CYP3A4 protein was strongly stimulated by the presence of δ-aminolaevulinic acid (ALA) in the growth medium (FIG. 7). Under these conditions ompA-3A4 yielded more spectrally active P450 compared to pelB-CYP3A4 (500 nmoles/l culture vs. 143 nmole/l culture respectively) even though the difference was less pronounced than expected from the immunoblot analysis. The presence of ALA in the culture medium led to the appearance of an absorption peak at 420 nm in the spectral analysis of the recombinant P450s (see FIG. 6, pelB-3A4 expressed in the presence of ALA and ompA-3A4 expressed in the absence of ALA).

Direct determination of the catalytic activity of the expressed proteins was not possible due to the absence of P450 reductase in bacterial membranes. The P450 enzyme activity was therefore determined in the presence of cumene hydroperoxide which serves as an artificial oxygen donor for P450s. In this analysis, we found that the turnover number of the pelB-CYP3A4 and the ompA-3A4 for the 6β-hydroxylation of testosterone was 4.2 $min^{-1}$ and 3.2 $min^{-1}$ respectively. These results clearly demonstrate that in *E. coli* these P450s fold correctly into spectrally and catalytically active enzymes.

Construction and Expression of CYP2D6 Fused to the ompA Leader Sequence

As we had found that the yield obtained for ompA-CYP3A4 was much higher than for the pelB-CYP3A4, we decided to fuse exclusively the ompA sequence to the N-terminus of CYP2D6, which is a P450 involved in the metabolism of a variety of therapeutically important compounds.

The PCR technique used for the fusion of the ompA signal sequence to the CYP2D6 cDNA was similar to the strategy used for the construction of the ompA-CYP3A4. This construct was expressed from the vector pCW. FIG. 8 displays an immunoblot of bacterial membranes obtained from *E. coli* harbouring the ompA-CYP2D6 cDNA construct (lane 2). An immunoreactive band corresponding to recombinant CYP2D6 was detected in these membranes, which was absent in membranes isolated from bacteria carrying the empty expression plasmid, pCW (lane 1). The ompA-CYP2D6 yielded a typical P450 $Fe^{2+}$ vs. $Fe^{2+}$—CO spectrum (FIG. 9). The yield of spectrally active CYP2D6 (481 nmoles/l of culture, FIG. 10) was similar to the yield achieved for ompA-CYP3A4 and resulted in a distinct red colouration of the bacteria expressing the former hemoprotein. The ALA dependent increase of spectrally active ompA-CYP2D6 was much stronger than for pelB-CYP3A4. In the presence of cumene hydroperoxide, ompA-CYP2D6 catalyzed the hydroxylation of the typical CYP2D6 substrate bufuralol with a turnover number of 50±3 $min^{-1}$.

Co-Expression of P450 and P450-reductase Fused to Bacterial Leader Sequences Generates a Functional Monooxygenase System in *E. coli*

In order to generate a functional P450-monooxygenase system, we tried to co-express P450 and P450-reductase in *E. coli*. It is possible to envisage three main ways to achieve co-expression of two proteins in *E. coli*. Firstly, two cDNAs can be expressed from separate compatible plasmids in the same cell: for example, P450 could be expressed from pCW and P450 reductase from a separate vector. Secondly, both cDNAs could be subcloned into the same plasmid. Thirdly, one or both of the cDNAs encoding P450 or P450 reductase could be integrated into the bacterial chromosome. We chose the first strategy, as it is technically least demanding.

The pelB-reductase cDNA was cloned into the vector pACYC184 (FIG. 3) to yield the vector pJR7. The advantage of this construct is that pACYC184 contains a different origin of replication from pCW. In addition these vectors contain different selection markers, which allow stable cotransformation with two separate plasmids, one for the expression of P450-reductase (pACYC184), the other (pCW) for expression of P450. E. coli were transformed with pJR7 and pCW carrying the ompA-CYP2D6 cDNA. Transformants were selected on ampicillin and chloramphenicol and expanded for further analysis. Immunoblotting (FIG. 8) revealed immunoreactive bands corresponding to the recombinant P450 reductase and CYP2D6 in membranes isolated from the co-expressing strains (lanes 3 and 4), which were both absent in membranes isolated from bacteria carrying the empty expression vector, pCW (lane 1). E. coli co-expressing ompA-CYP2D6 and the pelB-reductase displayed a typical $Fe^{2+}$ vs. $Fe^{2+}$—CO spectrum (FIG. 9). The total cellular yield of spectrally active ompA-CYP2D6 was 365 nmoles/l culture in the co-expressing strain which was only 25% lower than in E. coli expressing CYP2D6 alone (FIG. 10). Membranes containing the ompA-CYP2D6 and P450-reductase displayed a cytochrome c reductase activity of 530 nmoles/min/mg which is two fold higher than the value reported for human liver microsomes Most importantly intact bacteria co-expressing ompA-CYP2D6 and pelB-reductase as well as membranes derived from them catalyzed the hydroxylation of the typical CYP2D6 substrate bufuralol extremely efficiently with turn-over numbers of 4.6 $min^{-1}$ and 5.7 $min^{-1}$ respectively and a specific activity (1.2 nmoles/min/mg membrane protein) which was 40 fold higher than the value reported for human liver microsomes. The $V_{max}$ and the $K_m$ for the CYP2D6-catalyzed bufuralol 1'-hydroxylation were found to be 13.3 $min^{-1}$ and 11.1 µM respectively (FIG. 11).

Construction and Expression of CYP2A6 Fused to the ompA Signal Peptide

The ompA signal peptide was fused to the N-terminus of full-length CYP2A6 by PCR. The recombinant ompA-CYP2A6 expressed from pCW displayed a typical $Fe^{2+}$ vs. $Fe^{2+}$—CO difference spectrum in both whole cells and membranes derived from these cells (FIG. 13). The yield of spectrally active CYP2A6 in whole cells (193 nmol/l culture, FIG. 14) was somewhat lower than that of either CYP3A4 or CYP2D6 expressed from the analogous construct. Nonetheless, the specific CYP2A6 content of membranes isolated from these cells greatly exceeded the level which would be found in human liver microsomes.

Construction and Expression of CYP2E1 Fused to the ompA Signal Peptide

The same PCR-based strategy was used to fuse the ompA signal peptide to the N-terminus of full-length human CYP2E1. Expression from pCW resulted in the appearance of a protein in bacterial membranes which was detectable on immunoblotting using specific anti-CYP2E1 antibodies (FIG. 15, lane 3), and which was of the same apparent size as CYP2E1 in a sample of human liver microsomes (FIG. 15, line 1). This protein was absent in a sample of membranes isolated from E. coli carrying the empty expression plasmid, pCW (lane 2). The relative band intensities (cf. lanes 1 and 3) suggest that a very high level of recombinant CYP2E1 has been produced in this bacterial strain.

Furthermore, expression from pCW/ompA-CYP2E1 produced a typical reduced Fe—CO difference spectrum in whole bacterial cells (FIG. 16), although in this instance, the absorption maximum at around 420 nm was rather more pronounced than for the other P450-expressing constructs. The yield of spectrally active CYP2E1 in whole E. coli carrying pCW/ompA-CYP2E1 was estimated to be 451 nmol/l culture—approximately the same as the levels of CYP3A4 and CYP2D6 produced in whole cells from the analogous ompA-constructs.

Discussion

This Example demonstrates that a highly functional monooxygenase system in E. coli can be made by the fusion of P450s as well as P450 reductase to bacterial leader sequences such as pelB and ompA. This is clearly illustrated by the almost ten fold increase of functional P450 reductase levels obtained after fusion of the native P450 reductase to the pelB leader sequence and the expression of this construct from the vector pCW (FIG. 1). Expression of pelB-reductase from the vector pACYC 184, which we employed for the co-expression of P450s and P450-reductase, yielded P450-reductase levels in E. coli membranes similar to those found in human liver microsomes (100 pmol P450-reductase/mg protein). The applicability of our approach is not only limited to the expression of P450-reductase in E. coli, since we found that pelB-P450 reductase can also be expressed in S. typhimurium at levels similar to those achieved in E. coli (data not shown).

Moreover, we demonstrate that P450s fused to bacterial leader sequences can be efficiently expressed in E. coli without relying on the extensive modifications of P450 N-termini which previously had been thought to be essential for optimal P450 expression (Barnes et al (1991) Proc. Natl. Acad. Sci. USA 88, 5597-5601; Gillam et al (1993) Arch. Biochem. Biophys. 305, 123-131; Larson et al (1991) J. Biol. Chem. 266, 7321-7324). Our gene fusion approach is applicable for P450s belonging to different gene families, since we were able to show that CYP3A4, CYP2D6, CYP2A6 and CYP2E1 (FIGS. 5, 8 and 15) can all be expressed in E. coli using this strategy. Recently we have also extended this approach to the expression of CYP2C9 and CYP2D9.

Previously CYP3A4 and CYP2D6 cDNAs have been expressed in E. coli after modifications of their 5' ends in order to remove regions with the potential to form secondary structures (Gonzalez et al (1995) Annu. Rev. Pharmacol. Toxicol. 35, 369-390). These modifications translated into extensive changes in the N-terminal region of CYP3A4 and CYP2D6 (in the following these modified proteins are designated as 17α-CYP3A4 and 17α-CYP2D6 respectively). With respect to P450 yield our gene fusion strategy is superior to this approach, at least for the P450s which we have tried, since yields of ompA-CYP3A4 and of ompA-CYP2D6 expressed from the vector pCW were at least by a factor of 1.7 and 4.8 respectively higher than the published values for 17α-CYP3A4 and of 17α-CYP2D6 expressed from the same vector (FIG. 12). We strengthened this observation by repeating the expression of 17α-CYP3A4 and 17α-CYP2D6 from constructs which had been generated in our laboratory according to published procedures (Gillam et al (1993) Arch. Biochem. Biophys. 305, 123-131; Gillam et al (1995) Arch. Biochem. Biophys. 319, 540-550). We have expressed the pelB-CYP3A4 and the ompA-CYP3A4 with C-terminal extensions containing a stretch of histidine residues. We were able to purify mg quantities of these proteins for structural analysis using nickel agarose affinity chromatography.

We have extended our ompA leader fusion strategy to allow the expression of two further human cytochromes P450, namely CYP2A6 and CYP2E1, in *E. coli*. For CYP2E1, our expression level of 451 nmol/l culture (FIG. 16) is an order of magnitude greater than the previously published level of expression for this enzyme in *E. coli* (40 nmol/l, Gillam et al (1994) *Arch Biochem Biophys* 312, 59-66), using conventional sequence optimisation procedures. To our knowledge, the expression of CYP2A6 in *E. coli* has never before been reported. Hence, we have been able to demonstrate the simplicity and versatility of our system.

Most importantly we show that the gene fusion approach can be used to generate a highly functional human P450 monooxygenase system in *E. coli*. This is clearly demonstrated by the high bufuralol 1'-hydroxylase activity observed with intact *E. coli* co-expressing ompA-CYP2D6 and pelB-P450 reductase. This activity (1.2 nmoles/min/mg protein) is about 20 fold higher than the average bufuralol hydroxylase activity reported for a panel of human liver microsomes. Also bacterial membranes isolated from this *E. coli* strain display a similar high P450 enzyme activity. The ompA-CYP2D6 displays a higher substrate turnover number (4.6 min$^{-1}$) than the value calculated for human liver microsomes (1 min$^{-1}$) and also than the data reported for CYP2D6 reconstituted in an optimized cell free system. This result clearly demonstrates that ompA-CYP2D6 and the pelB-reductase couple very efficiently in *E. coli* and suggests that both proteins are located on the same side of the bacterial membrane in a phospholipid environment at least as optimal as the complex phospholipid compositions employed in reconstituted systems.

It is important to note that *E. coli* expressing ompA-CYP2D6 and pelB-reductase use endogenous NADPH as source for reducing equivalents, since they displayed P450 enzyme activity in the absence of exogenously added NADPH. This finding suggests that the reductase active site is located on the cytoplasmic side of the inner membrane where it is able to utilise the intracellular pool of NADPH. This property, combined with the high yield of recombinant protein and the technically simple maintenance, makes the system ideally suited for bioreactor purposes. However we have observed that P450 substrates are metabolized poorly by *E. coli* co-expressing P450s and P450 reductase when maintained in culture broth rather in the buffer used in the present study. This might indicate that under the former conditions, substrates were not able to penetrate the bacterial cell wall and membranes. We have therefore taken our strategy further and have expressed a functional P450 monooxygenase system in the TA series of *S. typhimurium* strains. These strains have frequently been used for mutagenicity testing, since they contain a deep rough mutation resulting in a permeable cell wall, which can be penetrated by a large panel of structurally diverse compounds (Ames et al (1975) *Mutat. Res.* 31, 347-364; Simula et al (1993) *Carcinogenesis* 14, 1371-1376). We were able to show that using our gene fusion strategy a functional P450-monooxygenase system could be generated in *S. typhimurium*.

We envisage that the P450 and P450-reductase expression levels in *E. coli* can be further increased using other vectors or other bacterial hosts. For example we have observed that some of the bacterially expressed ompA-CYP2D6 was malfolded and might have formed inclusion bodies. Recently *E. coli* strains have become available which express molecular chaperones and thioredoxin (Yasukawa et al (1995) *J. Biol. Chem.* 270, 25328-25331). The expression of these proteins, which prevent misfolding of newly synthesized proteins, resulted in a much higher yield for several recombinant proteins. These strains could be also used for the expression of P450s from expression vectors containing stronger bacterial promoters than pCW. For example we have observed that high levels of recombinant CYP3A4 can be expressed in *E. coli* under the control of the powerful T7 polymerase promoter in the pET series of vectors. However only a small fraction of the recombinant CYP3A4 was Spectrally active. Furthermore we envisage that the coupling of P450s with P450-reductase can be further improved by co-expression of the P450-reductase FMN domain which has been recently shown to stimulate the P450 enzyme activity in a reconstituted system containing P450 and P450 reductase.

In summary, we have developed a general approach for the efficient bacterial expression of P450s and demonstrated that this approach can be used to generate bacteria containing a highly functional P450 dependent monooxygenase system. These models will have important commercial applications in drug development and biocatalysis.

EXAMPLE 3

Expression in *Salmonella typhimurium*

Coexpression of P450 and P450s in certain *S. typhimurium* strains such as TA1538 and TA1535 is readily adapted from the *E. coli* system described above. The same vector system can be employed in both species. The vector is first passaged from the *E. coli* strains which are used for P450 expression (eg. JM109 or DH5α) through the *E. coli* strain LA5000 and from there to the *S. typhimurium* strains. However for the expression of P450s in the *S. typhimurium* strains TA98 and TA100, which are frequently used in mutagenicity testing, the strategy may have to be slightly modified. TA98 and TA100 carry the plasmid pKM101 which increases the SOS repair in these strains and concomitantly their sensitivity to mutagens. However this plasmid codes also for the ampicillinase. For the expression of P450s from the expression plasmid pCW in these strains, the ampicillinase marker on pCW has to be replaced by a tetracycline resistance marker. Otherwise growth conditions and induction of P450 expression in *S. typhimurium* is similar to the *E. coli* system. However, we have found that it is desirable to omit tetracycline from the growth medium during the P450 induction phase.

EXAMPLE 4

Expression of CYP3A4 and P450 Reductase in *Escherichia coli* and *Salmonella typhimurium* Strains With Altered Outer Membrane Permeability Materials and Methods Bacterial Strains and Plasmids The *E. coli* K12 strains used were JM109 (Yanisch et al (1985) *Gene* 33, 103-19), AB1157 (Howard-Flanders et al (1964) *Genetics* 49, 237-246) and NS3878 (Chaterjee and Sternberg (1995) *Proc. Natl. Acad. Sci.* 92, 8950-8954). The *S. typhimurium* strain was TA1535 (Ames et al (1975) *Mutat. Res.* 31, 347-352)). NS3678 is strain AB 157 tolC (λLP1) and the tolC mutation is due to a Tn10tet' insertion. TolC mutants are extremely sensitive to hydrophobic agents (Whitney (1970) *Genetics* 30, 39-59) and this protein is proposed to play a role in assembly of lipopolysaccharide (LPS) in the outer membrane (Schnaitmann and Klena (1993) *Microbiol. Rev* 57, 655,682). *S. typhimurium* strain TA1535 carries an rfa mutation and has a defective outer membrane. Co-expression of CYP3A4 and P450 reductase was achieved using the plasmid pB216 described in the previous examples.

Co-Expression of CYP3A4 and P450 Reductase

The protocol used for expression was identical to those previously described with the exception that for NS3678

[pB216] tetracycline (10 μg/l) was included in the streak plates and in tie overnight LB culture but not in the terrific broth. CYP3A4 content was determined in whole bacterial cells using $Fe^{2+}$—CO vs $Fe^{2+}$-difference spectra.

Incubation of Intact Cells With CYP3A4 Substrates

After the usual 20-24 hr induction, cells were cooled on ice for 10 minutes before harvesting by centrifugation. The cells were then washed once in an equal volume of ice cold 1×M9 salts solution before resuspending in ⅒ volume of M9+glucose (10 mM). Care was taken throughout not to subject the cells to vigorous pipetting. Cell suspensions were stored on ice until required for incubation with CYP3A4 substrates, 500 μl was removed and added to a 50 ml polypropylene tube containing 4.5 ml M9+glucose. The tubes were pre-incubated for 5-10 minutes in an orbital shaker at 37° C. before the reactions were initiated by addition of either testosterone or nifedipine at a final concentration of 200 μM. When required, 200 μl of cell suspension was removed and transferred to a 1.5 ml Eppendorf microcentrifuge tube containing 100 μl of methanol and 5 μl of 60% perchloric acid. The tubes were mixed by inversion and stored on ice for 10 minutes before centrifuging to remove precipitate. The supernatants were transferred to microvials for HPLC analysis. Metabolites were separated as previously described and the yield of 6β-OHT) or nifedipine oxide calculated by reference to known standards.

Results

CYP3A4 and P450 Reductase Expression in the Four Strains

Levels of P450 expression and P450 reductase activity are shown in Table A. CYP3A4 content in NS3678 [pB216] cells is significantly lower than in the other three strains, typically around 30 nmol/l. The reasons for this are unclear and expression in this strain will require further optimisation.

TABLE A

Expression levels of CYP3A4 in and CYP3A4-dependent metabolism of testosterone and nifedipine by intact JM109, AB1157, NS3678 and TA1535 pB216 cells

|  | P450 content (nmol/l culture) | Turnover (min$^{-1}$) | |
| --- | --- | --- | --- |
|  |  | Testosterone | Nifedipine |
| JM109 [pB216] | 105 ± 13 | 0.15 ± 0.11 | 1.38 ± 0.06 |
| AB1157 [pB216] | 80 ± 24 | 2.5 | 18.4 |
| NS3678 [pB216] | 32 ± 7 | 15.3 ± 12.3 | 17.8 ± 2.9 |
| TA1535 [pB216] | 119 ± 42 | 0.52 ± 0.14 | 5.4 ± 2.5 |

P450 contents were measured by $Fe^{2+}$—CO vs $Fe^{2+}$ difference spectra. Contents are expressed as means of at least 3 experiments±SD. Turnover numbers are recorded as nmol product formed/min/nmol P450, and are shown ±SD. The products detected were 6β hydroxytestosterone and nifedipine oxide.

Metabolism of Testosterone and Nifedipine by Intact E. coli and S. typhimurium Strains Expressing CYP3A4 and P450 Reductase The turnovers for testosterone and nifedipine by the four strains are shown in Table A. From previous work using JM109 [pB216] it had been shown that metabolism of testosterone was negligible unless the cells were resuspended in a buffer (TSE) containing EDTA and subsequently subjected to osmotic shock. This was confirmed here, the turnover after a 10 minute incubation being only 0.15 nmol 6β-OHT/nmol P450/min. In contrast testosterone metabolism in the other two E. coli strains were much more extensive, NS3678 [pB216] being particularly impressive with a turnover of 15.3 which is 100-fold higher than in JM109 [pB216]. The S. typhimurium strain TA1535 [pB216] also showed more activity than JM109 [pB216] towards testosterone but only by a factor of 3-4 fold. The turnovers for nifedipine followed a similar pattern although the inter-strain differences were not so marked as with testosterone. The E. coli strains NS3678 [pB216] and AB1157 [pB216] again showed the highest activity at around 18 nmol nifedipine oxide 1 nmol P450/min with turnovers for TA1535 [pB216] and JM109 [pB216] being around 3 and 15-fold lower respectively.

The results of time course incubations with the two substrates nifedipine and testosterone are shown in FIGS. 17 and 18 respectively. In the two most extensively metabolizing strains, AB1157 and NS3678, metabolite accumulation continues for 1-2 hours and with final concentrations of metabolite in the 30-40 μM range representing a yield of 20-30%. The loss of linearity after approximately one hour incubation may be due to loss of CYP3A4 or metabolite inhibition.

Discussion

Work described in the previous examples shows that JM109, the strain of E. coli routinely used for expression, was unable to catalyse testosterone hyroxylation when co-expressing CYP3A4 and reductase unless the cells were subjected to osmotic shock in TSE buffer. This lack of metabolism is almost certainly due to the impermeability of the E. coli outer membrane to large, hydrophobic molecules (Nikaido and Vaara (1985) *Microbiol. Rev* 49, 1-32) and makes this strain unsuitable for generation of large quantities of certain P450 metabolites in bioreactor systems. It is anticipated that outer membrane permeability will not be a problem for all P450 substrates, for instance we have found that turnover of 7-ethoxyresorufin in intact JM109 expressing CYP1A2 and P450 reductase is comparable to that in osmotically shocked cells (data not shown). E. coli strains such as NS3678 which carry a mutant tolC gene are known to be hypersensitive to hydrophobic agents and it was predicted that permeability to P450 substrates would also be increased. Based on the extremely high turnovers of testosterone and nifedipine by NS3678 [pB216] relative to JM109 [pB216] this seems to be the case. Currently, the P450 expression levels in strain NS3678 are relatively low. We envisage that these can be improved by optimisation of growth conditions. However, expression levels in the parent strain, AB1157 [pB216], are comparable to those in JM109 [pB216] with the advantage that substrate turnover is considerably higher. We believe that this is due to the rfbD1 mutation carried by this strain which confers a partially defective outer membrane. Our work represents the first example of expression of a functional P450 monooxygenase in "permeable" strains of E. coli. The system described here will be applicable for expression of all P450s and will facilitate the production of a wide range of P450 metabolites in "bioreactor" systems.

Summary

E. coli JM109 or DH5α which coexpressed P450s together with P450 reductase metabolised substrates only after treatment with buffer (TSE) which would alter the permeability of membranes. We have now expressed these enzymes in S. typhimurium TA1535 and in E. coli strains with a permeable cell wall. We were able to shown that, in the presence of a physiological broth (minimal medium+glucose), the metabolism of substrates is linear for more than 60 minutes at turnover rates which approach those found using cells resuspended in TSE buffer.

EXAMPLE 5

Co-Expression of ompA- and ompA (+2)-P450s with Reductase

Materials and Methods

Plasmids

Two P450 expression plasmids, pCW/ompA(+2)-CYP3A4 and pCW/ompA(+2)-CYP2A6, were constructed. In each case, PCR was used to insert a dipeptide "linker" (-Ala-Pro-), corresponding to the first two amino-acids of the mature OmpA protein, between the OmpA signal peptide and the P450 N-terminus. In order to allow facile purification of recombinant CYP3A4 by affinity chromatography (see below) for N-terminal sequence analysis, two further plasmids, pCW/ompA-CYP3A4(His)$_6$, and pCW/ompA(+2)-CYP3A4(his)$_6$ were also constructed, in which six histidine residues were appended to the C-terminus of the P450.

Co-Expression Methodology

The basic techniques for co-expression of P450 and reductase from separate compatible plasmids have already been described in the previous examples.

Coumarin 7-hydroxylate Assay membrane assays were carried out in 100 mM Tris-HCl (pH 7.4) containing 20 pmol CYP2A6, 50 µM coumarin, and a NADPH generating system (described previously in Example 1), in a total volume of 500 µl. Assays on bacterial cells were performed in TSE buffer in a total volume of 5 ml, and contained 50 pmol CYP2A6 per ml incubation, and 50 µM coumarin. Samples (500 µl) were withdrawn at intervals and analysed for metabolite formation. Processing of samples from cell and membrane assays was identical: reactions were stopped by the addition of 72 µl of 12.5% trichloroacetic acid, and were then placed on ice. Dichloromethane (1 ml) was then added, and the tubes vortexed vigorously. Following centrifugation to separate then two phases, the upper (aqueous) layer was discarded. An aliquot (500 µl) of the lower, organic phase was then transferred to a fresh tube containing 3 ml of 30 mM sodium borate buffer (pH 9.0). Tubes were then vortexed and centrifuged once more. The metabolite in the upper (aqueous) phase was then quantified fluorometrically, using excitation and emission wavelengths of 358 and 458 nm, respectively, by reference to authentic standard (umbelliferone, Sigma).

Purification of Recombinant P450 and N-terminal Sequence Analysis

Expression from pCW/ompA-CYP3A4(His)$_6$ and pCW/ompA(+2)-CYP3A4(His)$_6$ was carried out as previously described. Following lysozyme treatment of the cells and centrifugation, the splieroplasts were resuspended in binding buffer (20 mM potassium phosphate, pH 7.4, containing 500 mM potassium chloride and 20% glycerol (v/v)) and stored at −70° C. Spheroplasts deriving from 125 ml culture were typically resuspended in 9 ml buffer. For P450 purification, spheroplasts were thawed on ice and sonicated in the presence of the protease inhibitors aprotinin (1 µg/ml), leupeptin (1 µg/ml) and PMSF (1 mM), using a MSE SoniPrep 150 sonicator on 70% power. After centrifugation ($1.2 \times 10^4$ g, 12 min, 4° C.), the supernatant proteins were solubilised by stirring in the presence of Emulgen 911 (1 mg/mg protein) at 4° C. for 60 min. The mixture was clarified by centrifugation ($10^5$ g, 60 min, 4° C. (and then loaded onto a Hi-Trap chelating column (Pharmacia) which had been charged with nickel ions and then pre-equilibrated with binding buffer containing 0.10% Emulgen 911 (w/v). The column was washed with a further ten column volumes of binding buffer (containing Emulgen 911), and then weakly-binding proteins were removed with five column volumes of wash buffer (binding buffer containing 0.10% Emulgen 911 (w/v) and 75 mM imidazole). The red P450 band was eluted with elution buffer (binding buffer containing 0.10% Emulgen 911 (w/v) and 1 M imidazole)—the imidazole concentration was kept high to elute the P450 into as small a volume as possible. The protein sample was dialysed overnight at 4° C. against several changes of anion-exchange buffer (20 mM Tris-Cl, pH 7.5, containing 20% glycerol (v/v), 0.2 mM dithiothreitol, 1 mM EDTA and 0.10% Emulgen 911 (w/v)), and then loaded onto a Hi-Trap Q column (Pharmacia). The flow-through fraction, containing the P450, was then loaded onto an Econo-Pac® HTP cartridge (Bio-Rad) equilibrated with 10 mM sodium phosphate, pH 7.4, containing 20% glycerol (v/v), 1 mM EDTA, 1 mM DTT and 0.05% sodium chelate (w/v). The concentration of sodium phosphate was increased during column washing to 25 mM, and then to 100 mM, with the P450 eluting at 400 mM phosphate. The purity of the P450 preparation at each stage of the procedure was assessed by SDS-polyacrylamide gel electrophoresis, on 9% acrylamide (w/v) gels, straining with Coomassie Brilliant Blue R-250. The N-terminal sequencing, purified proteins were then transferred onto Pro-blot polyvinylidene fluoride membrane (Applied Biosystems) and stained. N-terminal amino acid sequence analysis was carried out in the Department of Biochemistry, University of Dundee, using a Model 476A instrument (Applied Biosystems), with four to six cycles of Edman degradation.

Results

Co-Expression of ompA-P450s With Reductase

As reported previously, the P450 expressed from pCW/ompA-CYP2D6 couples well with co-expressed reductase, catalysing typical CYP2D6-dependent activities (see Example 2). Turnover measured for ompA-CYP2D6 were, in general, slightly higher than those measured from the corresponding pCW/17α-CYP2D6 construct (data not shown).

We have since co-expressed a number of other ompA-P450s with reductase in *E. coli*, including CYP3A4 and CYP2A6. In contrast to CYP2D6, these two ompA-P450s do not appear to couple as efficiently with reductase as the corresponding 17α-P450s, since enzyme activities toward probe substrates are generally lower. For example, coumarin 7-hydroxylate activities in both cells and membranes are more than an order of magnitude lower with ompA-CYP2A6 compared with 17α-CYP2A6 (Table B). Similarly, for CYP3A4, testosterone 6β-hydroxylase activity in membrane fractions is reduced with the ompA-construct (Table C). It is interesting to note, however, that this difference between the two constructs is absent with a different probe substrate, nifedipine, us used (Table C). This emphasises the need to use several marker activities, wherever possible.

TABLE B

Yields and activities of CYP2A6 co-expressed with reductase in two plasmid system

| | | | *Coumarin 7-hydroxylate activity | |
|---|---|---|---|---|
| P450 construct | Cellular P450 yield (nmol/culture) | Membrane P450 content (nmol/mg protein) | Shocked cells (nmol/min/nmol P450) | Membranes (nmol/min/protein P450) |
| 17α-CYP2A6 | 147 ± 10 | 0.19 ± 0.06 | 0.75 ± 0.17 | 2.9 ± 0.5 |
| ompA-CYP2A6 | 41 | 0.17 | <0.02 | 0.11 |
| ompA(+2)-CYP2A6 | 137 ± 60 | 0.26 ± 0.11 | 0.29 ± 0.07 | 1.0 ± 0.2 |

Where possible, values are expressed as mean ± SD, based on at least three independent determinations.
Cytochrome P450 was quantified by $Fe^{2+}$-CO vs. $Fe^{2+}$ difference spectroscopy, in 100 mM Tris-HCl, pH 7.4, containing 20% (v/v) glycerol, 10 mM CHAPS and 1 mM EDTA.
*Probe activity for CYP2A6, measured fluorometrically.

In order to try and find an explanation for the relative lack of coupling of the ompA-P450s with reductase, six histidine residues were appended to the C-terminus of the P450 expressed from pCW/ompA-CYP3A4. This allowed facile purification of the recombinant protein by nickel chelate affinity chromatography (described in Materials and Methods). This revealed that the ompA-P450 was not undergoing the expected processing by bacterial signal peptidase, in that the signal peptide was being retained. This may reflect the general level of over-expression of the P450, since it is known that the availability of signal peptidase can be limiting, especially for hybrid precursors with low processing efficiencies (van Dijl et al. (1991) Mol. Gen. Genet. 227, 4048).

Another factor which strongly influences signal peptidase activity is the structure around the site of signal cleavage (Duffaud and Inoyue (1988) J. Biol. Chem. 263, 10224-10228; Barkocy-Gallagher et al. (1994) J. Biol. Chem. 269, 13609-13613), including the first few amino-acids after the signal peptide (Barkocy-Gallagher) and Bassford (1992) J. Biol. Chem. 267, 1231-1238; Nilsson and von Heijne (1992) FEBS Lett. 299, 243-246). Over-expression of proteins with non-cleavable signal peptides can completely block the translocation apparatus of the cell, leading to accumulation of protein precursors (Barkocy-Gallagher and Bassford (1992) J. Biol. Chem. 267, 1231-1238). For our constructs, the sequence immediately following the signal peptide is the CYP3A4 N-terminus. The amino-acid at position +1 relative to the site of cleavage will therefore be methionine, whereas alanine is strongly preferred in this position in bacterial genes (von Heijne (1986) Nucl. Acids Res. 14, 4683-4690).

We can therefore envisage three possible strategies for improving the probability of signal peptide removal. Firstly, the bacterial signal peptidase could be over-expressed from a separate, compatible plasmid, several of which have been described (van Dijl et al. (1991) Mol. Gen. Genet. 227, 4048; Dalbey and Wickner (1985) J. Biol. Chem. 260, 15925-15931; March and Inouye (1985) J. Biol. Chem. 260, 7206-7213). As an alternative to, or perhaps in conjunction with, this first approach, it may also be advisable to introduce a short "linker" sequence between the signal peptide and the P450, although there may be disadvantages with producing a P450 with a short N-terminal extension. Finally, we could try expression in a different bacterial strain, since this has also been shown to affect the extent of removal of signal peptides from hybrid fusion proteins (Monteilhet et al. (1993) Gene 125, 223-228).

In order to try and circumvent this problem of signal retention, we therefore decided to modify the cleavage site by introducing the first two amino acids of the mature OmpA protein (-Ala-Pro-) between the OmpA leader and the N-terminus of the P450. This resulted in the constructs pCW/ompA(+2)+CYP2A6 and pCW/ompA(+2)-CYP3A4 (described above). In contrast to the ompA-P450s, these ompA (+2)-P450s appeared to couple more efficiently with co-expressed reductase, resulting in higher substrate turnovers (Tables B and C). The recombinant protein expressed from pCW/ompA(+2)-CYP3A4(His)$_6$ was subsequently purified and subjected to N-terminal sequence analysis. This revealed that the protein was now being correctly processed by bacterial signal peptidase, leading to the accumulation in bacterial membranes of native CYP3A4 containing Ala-Pro- at the N-terminus.

TABLE C

Yields and activities of CYP3A4 co-expressed with reductase in two plasmid systems

| P450 construct | Cellular P450 yield (nmol/l culture) | *P450 content (nmol/mg protein) | *Reductase activity §(U/mg protein) | †Testosterone 6β-hydroxylase | †Nifedipine oxidase |
|---|---|---|---|---|---|
| 17α-CYP3A4 | 308 ± 43 | 0.36 ± 0.08 | 498 ± 30 | 4.9 ± 0.3 | 9.1 ± 0.7 |
| ompA-CYP3A4 | 374 ± 23 | 0.49 ± 0.06 | 313 ± 12 | 2.5 ± 0.8 | 8.8 |
| ompA-CYP3A4 | 292 ± 54 | 0.27 ± 0.05 | 535 ± 112 | 9.9 ± 0.2 | 11.1 ± 0.3 |

Where possible, values are expressed as mean ± SD, based on at least three independent experiments. Cytochrome P450 was quantified by $Fe^{2+}$—CO vs. $Fe^{2+}$ difference spectroscopy, in 100 mM Tris-HCl, pH 7.4, containing 20% (v/v) glycerol, 10 mM CHAPS and 1 mM EDTA.
*Measured in bacterial membrane fractions.
§one unit of reductase activity is defined as 1 nmol of cytochrome c reduced per minute.
†Metabolism of two known CYP3A4 substrates was assessed in membrane fractions in the presence of 30 mM $MgCl_2$. Activities are expressed as turnovers in nmol formed per minute per nmol CYP3A4.

Summary

The straight fusion of the ompA leader sequence to P450s does not always result in a P450 isoenzyme which couples with coexpressed reductase. Changing the amino acid residues at the potential cleavage site of the ompA sequence fused to the P450 sequence results in coupling and efficient removal of the leader sequence.

The invention claimed is:

1. A bacterial cell of family Enterobacteriaceae containing a spectrally active eukaryotic cytochrome P450 monooxygenase, comprising a genetic construct encoding, and capable of expressing, the spectrally active eukaryotic cytochrome P450 monooxygenase, wherein the spectrally active eukaryotic cytochrome P450 monooxygenase (i) has, at its N-terminal, a bacterial signal peptide, (ii) is capable of catalyzing oxidation of a substrate through insertion of one atom of molecular oxygen into the substrate, and (iii) is associated with an inner membrane of the bacterial cell, with an active site of the spectrally active eukaryotic cytochrome P450 monooxygenase located in a cytoplasm of the bacterial cell.

2. A composition comprising a plurality of bacterial cells according to claim 1, wherein each cell contains a genetic construct which encodes and is capable of expressing a different spectrally active eukaryotic cytochrome P450 monooxygenase.

3. The bacterial cell according to claim 1, wherein the spectrally active eukaryotic cytochrome P450 monooxygenase further comprises a peptide sequence which will aid purification of the spectrally active eukaryotic cytochrome P450 monooxygenase.

4. The bacterial cell according to claim 3, wherein the peptide sequence comprises a binding site for nickel.

5. The bacterial cell according to claim 4, wherein the peptide sequence is $-(His)_n$ where $n>4$.

6. The bacterial cell according to claim 1, wherein the spectrally active eukaryotic cytochrome P450 monooxygenase is selected from CYP1, CYP2, CYP3, or CYP4 families.

7. The bacterial cell according to claim 1, wherein the spectrally active eukaryotic cytochrome P450 monooxygenase is selected from CYP1A, CYP1B, CYP2A, CYP2B, CYP2C, CYP2D, CYP2E, CYP3A, CYP4A, CYP4B and subfamilies thereof.

8. The bacterial cell of claim 1 wherein the spectrally active eukaryotic cytochrome P450 monooxygenase is selected from CYP3A4, CYP2D6, CYP2C9, CYP2D9, CYP2A6 and CYP2E1.

9. The bacterial cell according to claim 1, wherein the bacterial signal peptide is ompA.

10. The bacterial cell according to claim 1, wherein the bacterial signal peptide is pelB.

11. The bacterial cell according to claim 1, wherein the bacterial signal peptide is malE.

12. The bacterial cell according to claim 1, wherein the bacterial signal peptide is phoA.

13. The bacterial cell according to claim 1, wherein the spectrally active cytochrome P450 monooxygenase is expressed at a level of at least 200 pmol/mg membrane protein.

14. A method of preparing isolated spectrally active eukaryotic cytochrome P450 monooxygenase, comprising
 (a) providing a sufficient quantity of cells according to claim 1; and,
 (b) isolating the spectrally active eukaryotic cytochrome P450 monooxygenase.

15. The method according to claim 14, wherein the spectrally active cytochrome P450 monooxygenase is expressed at a level of at least 200 pmol/mg membrane protein.

16. A genetic construct capable of expressing a spectrally active eukaryotic cytochrome P450 monooxygenase when introduced in a bacterial cell of family Enterobacteriaceae, wherein the spectrally active cytochrome P450 monooxygenase (i) has at its N-terminus a bacterial signal peptide, (ii) is capable of catalyzing oxidation of a substrate through insertion of one atom of molecular oxygen into the substrate, and (iii) is associated with an inner membrane of the bacterial cell, with an active site of the spectrally active eukaryotic cytochrome P450 monooxygenase located in a cytoplasm of the bacterial cell.

17. The genetic construct according to claim 16, wherein the spectrally active cytochrome P450 monooxygenase is expressed at a level of at least 200 pmol/mg membrane protein.

* * * * *

SEQUENCE LISTING

<160> NUMBER OF SEQ ID NOS: 6

<210> SEQ ID NO 1
<211> LENGTH: 22
<212> TYPE: PRT
<213> ORGANISM: Escherichia coli

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 2
<211> LENGTH: 21
<212> TYPE: PRT
<213> ORGANISM: Escherichia coli

<400> SEQUENCE: 2

Met Lys Lys Thr Ala Ile Ala Ile Ala Val Ala Leu Ala Gly Phe Ala
1               5                   10                  15

Thr Val Ala Gln Ala
            20

<210> SEQ ID NO 3
<211> LENGTH: 10
<212> TYPE: DNA
<213> ORGANISM: Escherichia coli

<400> SEQUENCE: 3
aggaggtcat                                                              10

<210> SEQ ID NO 4
<211> LENGTH: 96
<212> TYPE: DNA
<213> ORGANISM: Artificial Sequence
<220> FEATURE:
<223> OTHER INFORMATION: Recombinant cDNA

<400> SEQUENCE: 4
atgaaatacc tgctgccgac cgctgctgct ggtctgctgc tcctcgctgc ccagccggcg      60
atggccatgg atatcggatc cgaattccgc aacatg                                96

<210> SEQ ID NO 5
<211> LENGTH: 34
<212> TYPE: DNA
<213> ORGANISM: Artificial Sequence
<220> FEATURE:
<223> OTHER INFORMATION: Recombinant cDNA

<400> SEQUENCE: 5
tcgacagccc gcctaatgag cgggcttttt ttta                                   34

<210> SEQ ID NO 6
<211> LENGTH: 63
<212> TYPE: DNA
<213> ORGANISM: Escherichia coli

<400> SEQUENCE: 6
atgaaaaaga cagctatcgc gattgcagtg gcactggctg gtttcgctac cgtagcgcag      60
gcc                                                                     63